United States Patent
Hesketh et al.

(10) Patent No.: US 10,214,762 B2
(45) Date of Patent: Feb. 26, 2019

(54) CELL DIFFERENTIATION DEVICES AND METHODS

(71) Applicant: GEORGIA TECH RESEARCH CORPORATION, Atlanta, GA (US)

(72) Inventors: Peter J. Hesketh, Atlanta, GA (US); Douglas Britton, Atlanta, GA (US); Wayne D. Daley, Atlanta, GA (US); Alireza Mahdavifar, Atlanta, GA (US); Jie Xu, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 14/925,558

(22) Filed: Oct. 28, 2015

(65) Prior Publication Data
US 2016/0115519 A1   Apr. 28, 2016

Related U.S. Application Data

(60) Provisional application No. 62/069,378, filed on Oct. 28, 2014.

(51) Int. Cl.
*B01L 3/00* (2006.01)
*C12Q 1/10* (2006.01)

(52) U.S. Cl.
CPC .......... *C12Q 1/10* (2013.01); *B01L 3/502753* (2013.01); *B01L 3/502776* (2013.01); *B01L 2200/027* (2013.01); *B01L 2200/0636* (2013.01); *B01L 2200/0647* (2013.01); *B01L 2200/0694* (2013.01); *B01L 2300/069* (2013.01)

(58) Field of Classification Search
None
See application file for complete search history.

(56) References Cited

PUBLICATIONS

Lastoskie et al., Bio-,Micro-, and Nanosystems, ASM Conference 2003, p. 14 Abstract.*
Mao et al., PNAS, 2003, vol. 100, No. 9, p. 5449-5454.*
Long and Ford, Environ. Sci. Technol., 2009, vol. 43, p. 1546-1552.*
Diao et al., Lab Chip, 2006, vol. 6, p. 381-388.*
Gomez-Lopez et al., PloS One, 2011, vol. 6, issue 12, e28771, p. 1-8.*
Kim et al., Analyst, 2011, vol. 136, p. 3238-3243.*

* cited by examiner

*Primary Examiner* — Kade Ariani
(74) *Attorney, Agent, or Firm* — Troutman Sanders LLP; Ryan A. Schneider

(57) ABSTRACT

Methods, devices, and kits are provided for identifying, selecting, and/or manipulating live cells in a sample comprising a suspected mixed population of cells by subjecting the sample located in a first position to a linear gradient of a cellular stimulus to induce a change in a live cell sufficient to induce movement of the cell from a first position to a second position, wherein a dead cell, if present in the sample, is not induced to move to the second position in the presence of the cellular stimulus; and identifying or selecting the live cell in the second position.

18 Claims, 18 Drawing Sheets

Original image     Processed image     Detected bacteria (a) L-Aspartic Acid experiment a.1 Attractant side (b) Ni ion Experiment b.1 Repellent side (c) Control Experiment c.1 buffer side 1

(a) L-Aspartic Acid experiment a.2 buffer side (b) Ni ion Experiment b.2 buffer side (c) Control Experiment c.2 buffer side 2

A

B

CELL DIFFERENTIATION DEVICES AND METHODS

CROSS-REFERENCE TO RELATED APPLICATIONS

This application claims priority to U.S. Provisional Patent Application No. 62/069,378, filed Oct. 28, 2014, which is incorporated herein by reference in its entirety.

BACKGROUND

Food-borne disease remains a substantial burden on the public health. It is estimated that each year roughly 1 in 6 Americans (or 48 million people) get sick, 128,000 are hospitalized, and 3,000 die of foodborne diseases. See CDC. *Estimating Foodborne Illness: An Overview* (2014). Non-typhoidal *Salmonella enterica* and *Escherichia coli* 0157:H7 include two of the top pathogens contributing to domestically acquired foodborne illnesses resulting in hospitalization. Pathogen prevalence in food varies significantly. For example, the percentage of *Salmonella*-positive birds and fecal samples on farms has ranged from 5 to 100% (Foley, S. L., et al., J Anim Sci, 2008. 86(14 Suppl): p. E149-62), and 3 to 17% of pathogen-positive products can be found on fresh produce on farms (Strawn, L. K., et al., Applied and Environmental Microbiology, 2013. 79(2): p. 588-600).

Food production practices have developed many intervention strategies including the physical and chemical methods to reduce the contamination from the well-recognized food-borne pathogens such as *S. enterica* and *E. coli*. In order to maintain control of our food production system, the ability to rapidly detect the presence of viable pathogens along the production chain is essential for determining intervention and control strategies.

Current rapid approaches based on the immunoassays or nucleic acid detection assays are unable to distinguish between viable and non-viable pathogens (without an enrichment step) as most production processes have the inherent ability to provide some control. One key point in this is identifying the presence of live pathogens along the processing chain to evaluate risk and institute corrective measures.

Ethidium monoazide (EMA) and propidium monoazide (PMA) have been used to prevent the DNA amplification from the dead bacterial cells. They specifically permeate dead cells and irreversibly attach covalently to the DNA to prevent amplification. See, e.g., Yang, X., et al., Food Microbiology, 2011. 28(8): p. 1478-1482; Melero, B., et al., Food Microbiology, 2011. 28(7): p. 1353-1358; Taskin, B., A. et al., Appl. Environ. Microbiol., 2011. 77(13): p. 4329-4335; Chen, S., et al., Appl. Environ. Microbiol., 2011. 77(12): p. 4008-4016; Liang, N., et al., Journal of Food Science, 2011. 76(4): p. M234-M237. However, the degree of deactivation is limited to the presence of no more than $10^3$ dead cells in the PCR. See, e.g., Soejima, T., Analytical Biochemistry, 2011. 418(2): p. 286-294. Reverse transcriptase PCR (RT-PCR) was adapted to detect the less environmentally stable messenger RNA (mRNA) in bacteria so live cells detection can be achieved. See, e.g., Martínez-Blanch, J., et al., European Food Research and Technology, 2011. 232(6): p. 951-955; Cobo Molinos, A., et al., Current Microbiology, 2010. 61(6): p. 515-519. However, costs, complexities, and other technical issues have made neither a routine diagnostic tool.

Fluorescence microscope and flow cytometry have also been used to distinguish the viable cells from the dead cells. These methods utilize a fluorescent dye exclusion method to evaluate cell viability. Typical viability dyes are excluded by viable cells but can penetrate damaged cell membranes of dead cells and emit fluorescence upon binding to nucleic acid inside these cells. Single cell analysis of cell viability and MP typically has relied on staining procedures with fluorescence dyes. However, usage of fluorescence dyes with bacteria is not simple. Due to large interspecies variation, staining and measurement protocols have to be developed separately for every bacterial species to ensure qualitative and quantitative high level results. See, e.g., David, F., et al., Biotechnology and Bioengineering, 2012. 109(2): p. 483-492. In addition, some cells may be still structurally intact though dead (e.g., after being killed with UV light and antibiotics). See, e.g., Trevors, J. T., Journal of Microbiological Methods, 2012. 90(1): p. 25-28; Soejima, T., et al., Biochimica et Biophysica Acta (BBA)—General Subjects, 2012. 1820(12): p. 1980-1986. Moreover, some cells with injured cell membrane may repair and retain viability. See, e.g., Corrotte, M., et al., Traffic, 2012. 13(3): p. 483-494; Soejima, T., et al., FEMS Microbiology Letters, 2009. 294(1): p. 74-81. ENREF 19 Therefore, assays based on the cell membrane integrity may not be accurate enough to differentiate live from dead cells.

Separations of viable cells from the dead population have also been explored using dielectrophoresis, defined as the motion of polarizable particles exposed to a non-uniform electric field. See, e.g., Lapizco-Encinas, B. H., et al., Analytical Chemistry, 2004. 76(6): p. 1571-1579; van den Driesche, S., et al., Sensors and Actuators B: Chemical, 2012. 170(0): p. 207-214; van den Driesche, S., et al., Procedia Engineering, 2011. 25(0): p. 705-708. ENREF 17 The separation is based on the difference in cell membrane conductivity. The conductivity of viable cell membranes tends to be $10^{-4}$ μS/mm. When a cell dies, the cell membrane becomes permeable, and its conductivity can increase by a factor of $10^4$. See, e.g., Lapizco-Encinas, B. H., et al., Analytical Chemistry, 2004. 76(6): p. 1571-1579. This method again is based on the cell membrane integrity, which could generate false signal from the structurally intact but dead cells.

As such, the food processing industry is interested in technologies or methods that can quickly and accurately detect viable (live) bacteria, as these are the pathogens that can cause illness. Common foodborne pathogen screening methods like PCR (polymerase chain reaction) use DNA-based methods to perform the detection. However, because both viable (live) and non-viable (dead) bacteria contain the same DNA and other properties, it is difficult to distinguish between them without performing additional time-consuming incubation and culturing steps.

It is with respect to these and other considerations that the various embodiments described below are presented.

SUMMARY

In certain embodiments, a method is provided for manipulating live cells in a sample comprising a suspected mixed population of cells, comprising (a) subjecting the sample located in a first position to a linear gradient of a cellular stimulus to induce a change in a live cell sufficient to induce movement of the cell from a first position to a second position, wherein a dead cell, if present in the sample, is not induced to move to the second position in the presence of the cellular stimulus; and (b) identifying or selecting the live cell in the second position. In frequent embodiments, step (a) occurs in a microfluidic device. Also frequently, the first position comprises a laminar flow of the sample in a microfluidic channel, and the second position comprises: a chamber formed adjacent to the laminar flow path of the sample that is in direct fluid communication with the microfluidic channel, or a second laminar flow in the microfluidic channel. Often, the suspected mixed population of cells comprises bacterial cells. Also often, the linear gradient of the chemoeffector is produced via axial flow of the chemoeffector through a porous substrate.

In certain embodiments, a microfluidic device is provided comprising: a porous substrate adapted to support axial flow and a fluid impermeable substrate; a plurality of separate microfluidic channels formed in the porous substrate or fluid impermeable substrate, each defining a fluid flow path, wherein at least one of the plurality of separate microfluidic channels is in axial flow connection with at least one other of the plurality of separate microfluidic channels; and a chamber formed adjacent to the fluid flow path in the microfluidic channel and in direct fluid communication with the microfluidic channel.

Also in certain embodiments, a microfluidic device is provided comprising: a porous substrate adapted to support axial flow and a fluid impermeable substrate; and a plurality of separate microfluidic channels formed in the porous substrate or fluid impermeable substrate, comprising (a) a sample channel having a dual laminar flow path having a first and a second fluid inlet, and a first and a second fluid outlet; and (b) at least one chemoeffector channel, wherein the at least one chemoeffector channel is in axial flow connection with the sample channel through the porous substrate.

Also in certain embodiments, a modular microfluidic device is provided, comprising: a first and second fluid impermeable substrate, wherein the first impermeable substrate comprises an optically transparent portion and a fluid port; and a porous substrate removably positioned between the first and second fluid impermeable substrates, wherein the porous substrate is adapted to support axial flow and comprising a microfluidic channel formed in the porous substrate defining a fluid flow path, and wherein the first and second fluid impermeable substrates are coextensive along the fluid flow path.

In certain embodiments, a method of providing a linear chemical gradient in a microfluidic device unaffected by adjacent fluid flow is provided, comprising: (a) introducing an assay fluid to an upstream end of a microfluidic channel comprising a chamber of the device described herein to provide a fluid current of the assay fluid between the upstream end and a downstream end of the microfluidic channel, and (b) introducing a chemical of interest to another of the plurality of microfluidic channels in axial flow communication with the microfluidic channel of (a), and permitting the chemical to diffuse to the chamber through the porous substrate and mix with the fluid in the chamber, thereby producing the linear chemical gradient.

Also in certain embodiments, a method of separating cells in a sample based on a chemotaxic response is provided, comprising: (a) introducing a fluid containing a chemical stimulus to the at least one chemoeffector channel of the microfluidic device described herein and establishing a linear chemical gradient of the chemical stimulus within the sample channel through diffusion of the chemical stimulus across the porous substrate; (b) introducing a sample fluid containing a cell capable of exhibiting a chemotaxic response to the first fluid inlet, and introducing a second fluid to the second fluid inlet, whereby the dual laminar flow in the sample channel is comprised of the sample fluid as a first laminar flow path and the second fluid as a second laminar flow path, wherein the cell is exposed to the linear chemical gradient and is chemotaxically induced to move from the first laminar flow path to the second laminar flow path.

Also in certain embodiments, a method of separating cells using the microfluidic device described herein is provided, wherein the device comprises a first and a second chemoeffector channel, the method comprising: (a) introducing a fluid containing a chemorepellent to the first chemoeffector channel, introducing a fluid containing a chemoattractant to the second chemoeffector channel, and establishing a linear chemical gradient of the chemical stimulus within the sample channel through axial flow of the chemorepellent and the chemoattractant across the porous substrate; (b) introducing a sample fluid containing a cell capable of exhibiting a chemotaxic response to the first fluid inlet, and introducing a second fluid to the second fluid inlet, whereby the dual laminar flow in the sample channel is comprised of the sample fluid as a first laminar flow path and the second fluid as a second laminar flow path, wherein the first chemoeffector channel is positioned adjacent the first laminar flow path, and second chemoeffector channel is positioned adjacent the second laminar flow path, wherein the cell is exposed to the linear chemical gradient and is chemotaxically induced to move from the first laminar flow path to the second laminar flow path.

Also in certain embodiments, a method of separating cells in a sample based on a chemotaxic response is provided, comprising: (a) introducing a sample containing a cell within a sample channel of a microfluidic device and within a laminar flow of the sample channel; (b) exposing the cell in the sample channel to a chemical stimulus comprising a linear chemical gradient provided through axial flow of the chemical stimulus from at least one side channel, wherein: (i) the linear chemical gradient is provided within a static fluid chamber, the static fluid chamber positioned adjacent to the laminar flow of the channel, and separating the cell based on its movement in response to the chemical stimulus, wherein the movement is unaffected by the laminar flow of the assay fluid within channel; or (ii) the laminar flow comprises a dual laminar flow path comprising an sample fluid flow path and a second fluid flow path, and separating the cell based on its movement in response to the chemical stimulus, wherein the movement is a movement of the cell from the sample fluid flow path to the second fluid flow path.

Often, the cellular stimulus comprises a chemical, an electric field, or a temperature gradient. Also often, the chemical comprises a chemoeffector.

In frequent embodiments, the porous substrate has a pore size of less than 1.0 µm. Also frequently, the porous substrate has a pore size of less than 0.5 µm. Often, the porous substrate has a pore size less than the size of an analyte of interest to be evaluated on the device such that the analyte of interest is not capable of axial flow through the porous substrate.

In frequent embodiments, the device comprises three or more separate microfluidic channels. Often, the device comprises at least two chambers formed in at least one microfluidic channel. Frequently, the device comprises between two to eight chambers formed in one of the three of more separate microfluidic channels. Often, the device comprises 6 chambers, which are often situated on opposite sides of the channel.

In frequent embodiments, the chemical of interest comprises a chemoattractant or a chemorepellent. Often, methods provided herein comprises introducing a sample containing a cell to the assay fluid; exposing the cell to the linear chemical gradient of the chemoattractant or the chemorepellent; and separating the cell based on its movement in response to the chemical stimulus, wherein the movement is unaffected by the fluid current.

Often, the chemoattractant comprises aspartic acid, the chemorepellent comprises a nickel ion, and the cell comprises an *E. coli* cell.

In certain frequent embodiments the dual laminar flow path is defined by two separate laminar flow paths comprising: a first flow path corresponding to fluid introduced to the device at the first fluid inlet and exiting at the first fluid outlet; and a second flow path corresponding to fluid introduced to the device at the second fluid inlet and exiting at the second fluid outlet.

Often, the present devices comprise a first and a second chemoeffector channel, and wherein the first chemoeffector channel is positioned adjacent the first flow path, and second chemoeffector channel is positioned adjacent the second flow path.

In certain frequent embodiments, the chemical stimulus is a chemoattractant, and the movement is toward a higher concentration of the chemoattractant in the assay fluid.

Often, the microfluidic channel comprises a plurality of separate microfluidic channels formed in the porous substrate, each defining a fluid flow path, wherein at least one of the plurality of separate microfluidic channels is in axial flow connection with at least one other of the plurality of separate microfluidic channels.

Also often, the device further comprises a chamber formed adjacent to the fluid flow path in the microfluidic channel and in direct fluid communication with the microfluidic channel. Frequently, the device further comprised a chamber formed adjacent to the fluid flow path in the microfluidic channel and in direct fluid communication with the microfluidic channel.

These and other embodiments, features, and advantages will become apparent to those skilled in the art when taken with reference to the following more detailed description of various exemplary embodiments of the present disclosure in conjunction with the accompanying drawings.

BRIEF DESCRIPTION OF THE DRAWINGS

The skilled person in the art will understand that the drawings, described below, are for illustration purposes only.

DETAILED DESCRIPTION OF THE VARIOUS EMBODIMENTS

Figure 1:
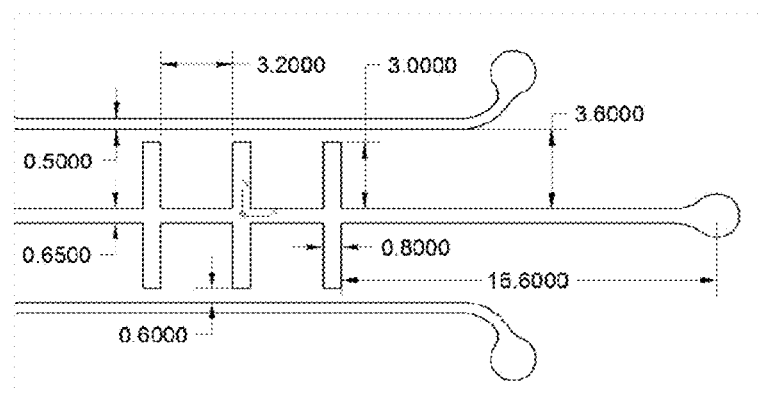
FIG. 1 depicts exemplary geometry of channels and chambers present in a porous substrate (e.g., nitrocellulose membrane) of an exemplary device. In an exemplary embodiment, the thickness of the channels and chambers is 120 μm normal to the plane.
Figure 1:
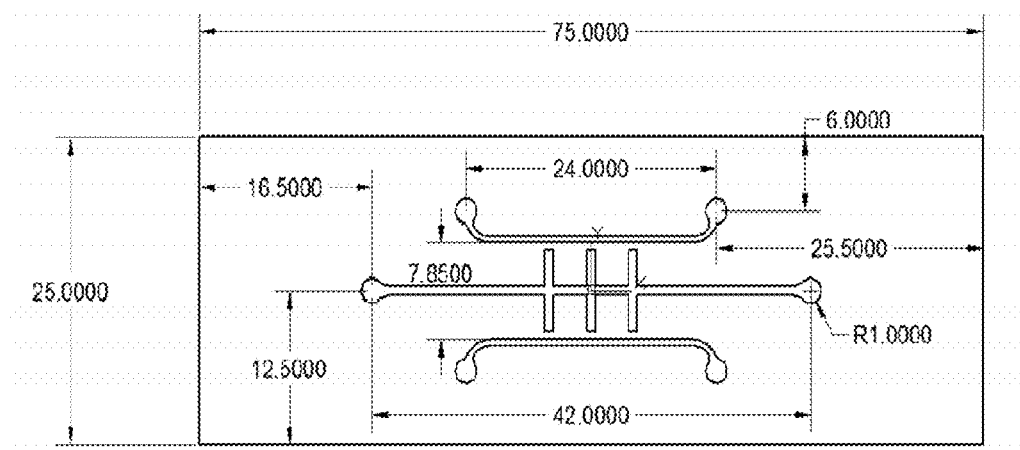

For clarity of disclosure, and not by way of limitation, the detailed description of the various embodiments is divided into certain subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "and/or" may mean "and," it may mean "or," it may mean "exclusive-or," it may mean "one," it may mean "some, but not all," it may mean "either," "neither," or it may mean "both."

As used herein, "subject" often refers to an animal, including, but not limited to, a primate (e.g., human). The terms "subject" and "patient" are used interchangeably herein.

As used herein, the terms "detect," "detecting," or "detection" may describe either the general act of discovering or discerning or the specific observation of a cell, molecule, or composition, whether directly or indirectly labeled with a detectable label.

As used herein, the phrase "live cell" or "viable cell" refers to an intact cell that maintains activity of at least a portion of its typical intracellular processes or extracellular reactions, such as flagella activity. Typically, these terms exclude lysed or fixed cells.

As used herein, "sample" refers to any substance containing or presumed to contain a cell of interest or a cell for investigation. The term "sample" thus includes a cell, organism, tissue, fluid, or substance including but not limited to, for example, blood, plasma, serum, spinal fluid, lymph fluid, synovial fluid, urine, tears, stool, external secretions of the skin, respiratory, intestinal and genitourinary tracts, saliva, blood cells, tumors, organs, tissue, samples of cell culture constituents, natural isolates (such as drinking water, seawater, solid materials), microbial specimens, cell lines, and plant cells. Often, a target cell is present or suspected to be present in a sample.

"Fluid sample" refers to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay. Typically, the sample is an aqueous solution or biological fluid as described in more detail below.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, buffer exchange or centrifugation of culture or cell-containing medium, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte.

The selection and pretreatment of biological, industrial, and environmental samples prior to testing is well known in the art and need not be described further.

"Axial flow" as used herein refers to lateral, vertical or transverse fluid flow or diffusion through a material such as a porous substrate. "Diffusion" (also referred to herein as "diffusive flow") through the material is intended to be included in the definition of axial flow. The type of flow contemplated in a particular device, assay, or method varies according to the structure of the device. Without being bound by theory, lateral, vertical or transverse flow may refer to flow of a fluid sample from the point of fluid contact on one end or side of a particular material supporting axial flow (the upstream or proximal end) to an area downstream (or distal) of this contact. The downstream area may be on the same side or on the opposite side of the matrix from the point of fluid contact.

"Bibulous" materials include paper, nitrocellulose, nylon and the like, which have the capability to effect a chromatographic separation of the contained materials.

"Non-bibulous" flow is meant liquid flow in which all of the dissolved or dispersed components of the liquid are carried at substantially equal rates and with relatively unimpaired flow through the membrane, as opposed to preferential retention of one or more components as would occur, for example, in materials capable of adsorbing or "imbibing" one or more components chemically, physically, ionically, or otherwise. Porous membranes amenable to non-bibulous flow include nitrocellulose, for example, which can provide non-bibulous flow by treating it with blocking agents that can block the forces which account for the bibulous nature of bibulous membranes. Preferably the interfering sites on the untreated bibulous membranes are completely blocked with the blocking agent to permit non-bibulous flow there through.

As used herein, "porous substrate" refers to a material such as a matrix, membrane, porous structure, or porous microstructure capable of supporting chemical diffusion, bibulous, or non-bibulous fluid flow therethrough. Nitrocellulose and polydimethylsiloxane (PDMS) represent a couple of types of porous substrate capable of supporting axial flow, as contemplated herein. For example, PDMS may be prepared through soft lithography techniques, e.g., having a controlled pore size and controlled dimensions (e.g., height). Pore size or pore structure size of the porous substrate is often less than the size of a target cell under investigation but large enough to permit diffusion of a chemical such as a chemoeffector (e.g., less than about 1 $\mu$m, about or less than 0.9 $\mu$m, about or less than 0.8 $\mu$m, about or less than 0.7 $\mu$m, about or less than 0.6 $\mu$m, about or less than 0.5 $\mu$m, or about or less than 0.5 $\mu$m, etc.) when it is desired to prohibit the cell from flowing through the porous substrate.

As used herein the terms "upstream" and "downstream" refer to the direction of fluid sample flow subsequent to contact of the fluid sample with a representative device of the present disclosure, wherein, under normal operating conditions, the fluid sample flow direction runs from an upstream position to a downstream position in a channel, chamber, or porous substrate.

As used herein, "fluid communication" refers to the disposition or arrangement of a material or materials such that fluid is able to flow through the material, flow between materials, or pass between zones or materials, for example via laminar flow, capillary action, bibulous flow, or non-bibulous flow. A material can be in "fluid communication" with another material regardless of the presence of fluid if it provides the capability to permit the flow of fluid between materials when fluid is present. In certain embodiments herein, the phrase "direct fluid communication" refers to fluid communication excluding axial flow.

As used herein, "separate microfluidic channels" or "separate channels" refers to independent channels, each formed in a material, or bounded by a material, such as a porous substrate, which channels are not directly connected. Such separate channels may be, when specified, in axial flow fluid communication with one-another through a porous substrate. In a device separate microfluidic channels may exist with certain channels directly connected or having a common origin or other point, when at least one other channel is present that is not directly connected with at least one other channel, except via axial flow connection. Flow within the channel is generally not axial fluid flow. Flow of fluid (e.g., assay fluid such as buffer, optionally containing a cell) within the channel often comprises laminar flow or microfluidic fluid flow, which is also referred to herein as a fluid current, current, bulk flow, or similar terms.

As used herein, "chamber" refers to a side extension (e.g., a channel, cavity, pocket, etc.) in fluid communication. Most frequently, a "chamber" refers to a side extension of a channel that lies in fluid communication with the channel, but outside of the flow path, e.g., laminar flow path, in that channel. Most frequently, fluid flow or stillness in at least a portion of the chamber is not disturbed or turbulently affected by the fluid flow in the channel (assuming sufficient fluid volume to fill the channel and chamber). It is this unagitated portion of the chamber often subjected to analysis according to the presently described methods and devices. Chambers, as contemplated herein, may assume a variety of orientations and/or shapes relative to the channel to which they are connected. In certain embodiments, a chamber comprises a side extension extending perpendicularly to the channel flow path. Most frequently, a channel comprises a plurality of chambers (e.g., 2, 3, 4, 5, 6, 7, 8, 9, 10, etc.), often situated on different sides of the channel.

As used herein "chemoeffector" refers to a chemo-attractant or a chemo-repellent, and is also referred to herein as a chemical stimulus. Chemoeffectors are determined or selected relative to an analyte under investigation. For example, if the analyte is a cell such as E. coli O157:H7, chemoeffectors may be selected from a broad group including aspartic acid (chemo-attractant) and a nickel ion containing composition such as $NiCl_2$ (chemo-repellent). The phenomenon known as "chemotaxis" is the movement of an organism in response to a chemical stimulus. For example, live bacteria naturally sense nutrient molecules such as sugars and amino acids as chemoeffectors/chemoattractants and move toward them.

The following detailed description should be read with reference to the drawings. The drawings, which are not necessarily to scale, depict selected embodiments and are not intended to limit the scope of the present disclosure. The detailed description illustrates by way of example, and is not intended to limit the scope of the present disclosure.

Chemotaxis

Researching bacterial chemotaxis can lead to a better understanding of bacteria toxicity (Hardoyo, et al., *Biotechnol Tech* 1993, 7(7):457-462) and to the development of improved strategies to treat bacterial infections. Bacterial chemotaxis is an impressive specific mechanism used by microorganisms for recognition of and response to environmental changes so the optimum environmental conditions to preserve their species and living systems can be discovered. See, e.g., Jeong H-H, et al., *Biosensors and Bioelectronics* 2013, 47:278-284. In the homogeneous environments, bacteria swim in a random walk composed of alternating straight runs, produced by counterclockwise (CCW) rotation of the flagellar rotary motor and tumbles, produced by clockwise (CW) rotation. See, e.g., Alder J, *Science* 1966, 153:708-716; Alder J, *Science* 1969, 166:1588-1597; Armitage J P, Schmitt R, *Microbiology* 1997, 143(12):3671-3682. However, in non-homogeneous environments, bacteria detect chemicals and direct cell movement up or down a chemical gradient in response to an attractant or repellent, respectively. The direction of flagella rotation is controlled by a sensory system that relays information from the environment surrounding the cell to the flagella. See, e.g., Koshland D E, et al., *Cold Spring Harbor Symp Quant Biol* 1988, 53 (Mol. Biol. Signal Transduction, Pt. 1):11-17.

The cytoplasmic side of membrane bound MCP (methyl accepting chemotaxis proteins) receptors detect changes in the concentration of the extracellular chemoeffectors through the ligand binding, which in turn leads to the modulation of the methylation state of MCPS and results a conformation change. MCP receptors are bound to autophosphorylating histidine kinase CheA through protein CheW. The "kinase on" receptor conformation (increase of repellant) stimulates the CheA autophosphorylation rate several hundred-fold, whereas the "kinase-off" conformation (increase of attractant) deactivates CheA autophosphorylation. See, e.g., Hazelbauer G L, et al., *Trends in Biochemical Sciences* 2008, 33(1):9-19. Next, the cellular signal is relayed from CheA to flagellar-motor-binding protein, CheY through the phosphoryl group shift. In response to phospho-CheY (CheY$^P$), the rotary motors switch to CW rotation, resulting in a tumble. CheA autophosphoralation is inhibited upon chemoattractant binding to receptors. This reduces CheY$^P$ and tumble frequency, thus increasing the length of a biased smooth run. See, e.g., id; Greenfield D, et al., *PLoS Biol* 2009, 7(6):e1000137.

Bacterial chemotaxis is closely related to microbial metabolism, biofilm formation, cell to cell signaling, contaminant bioremediation, and disease pathogenesis. See, e.g., Auletta G, *Entropy* 2013, 15(1):311-326; Yaryura P M, et al., *Current Microbiology* 2008, 56(6):625-632; Eisenbach M, et al., *Chemotaxis: Imperial College Press;* 2004; Krell T, et al., *Current Opinion In Biotechnology* 2013, 24(3):451-456; Lux R, Shi W, *Critical Reviews in Oral Biology & Medicine* 2004, 15(4):207-220. Using a home-made microscope, in 1676 Anton van Leeuwehoek first observed and described bacteria motility. His findings set the stage for future methods developed to study chemotactic behavior and quantify motility. In the late 1800s, Wilhelm Pfeffer created a capillary assay to study the response of bacteria to nutrients. See Pfeffer W: *Unters Botan Inst Tubingen* 1888, 2:582-661. This method was later improved and standardized by Julius Adler. See Adler J, *J Gen Microbiol* 1973, 74(Pt. 1):77-91. Adler also introduced the swarm plate assay, which is a relatively simple way to separate non-chemotactic mutants and qualitatively study chemoeffector response. See, e.g., Alder J, *Science* 1966, 153:708-716. Both methods were instrumental in identifying cell-surface chemoreceptors and determining attractant amino acids and other compounds. See, e.g., Hazelbauer G L, et., *PNAS* 1969, 64(4):1300-1307; Mesibov R, Adler J, *Journal of Bacteriology* 1972, 112(1):315-326. Adler's fundamental and significant discoveries published in the mid-1960s systematically described the chemotactic components and their roles in *E. coli*, this was a turning point in the understanding of bacterial chemotaxis.

The pioneering work done by Adler caught the attention of many other scientists and led to the development of the temporal gradient assay, and three-dimensional tracking Temporal gradient assays quantify bacterial migration by introducing either an attractant or repellent creating an abrupt step in concentration. See, e.g., Macnab R M, Koshland D E, *PNAS* 1972, 69(9):2509-2512. In the early 1970s Howard Berg designed and built an automated microscope to track single cell movement and chemotactic behavior. His observations led to the discovery of the 3D random walk and the biased random walk. See, e.g., Berg H C, *Review of Scientific Instruments* 1971, 42(6):868-871; Berg H C, Brown D A, *Nature* 1972, 239(5374):500-504.

The unique features of microfluidics have recently proven to be useful for the investigation of bacterial chemotaxis. See, e.g., Dertinger S K W, et al., *Anal Chem* 2001, 73(6): 1240-1246; Diao J, et al., *Lab Chip* 2006, 6(3):381-388; Lin F, et al., *Lab on a Chip* 2004, 4(3):164-167. A microfluidic system provides, in theory, a laminar flow, a large surface-to-volume ratio, a flexible range of concentration gradients, and in a high throughput ideally resulting in a fast, sensitive, accurate and reproducible chemotaxis analysis. In 2003 Mao et al were the first to use a microfluidic device to study chemotaxis. See, e.g., Englert D L, et al., *Methods Mol Biol* (Totowa, N.J., US) 2009, 571 (Chemotaxis):1-23; Mao H, et al., *Proceedings of the National Academy of Sciences* 2003, 100(9):5449-5454. Their design involved a bacteria stream sandwiched between two laminar flows containing the chemoeffectors (also referred to as chemical stimulus). The chemical gradients from the chemoeffectors were established by means of diffusion. The cells in the center stream sensed the chemical gradient and made the corresponding shift in the trajectory. A variety of microfluidic designs have been recently developed to generate a stable chemical gradient. See, e.g., Ahmed T, S et al., *Integrative Biology* 2010, 2(11-12):604-629; Lanning L M, et al., *Biotechnology and Bioengineering* 2008, 100(4):653-663; Saadi W, et al., *Biomedical Microdevices* 2007, 9(5):627-635. These studies demonstrate the power and potential of microfluidic approaches for chemotaxis studies, yet none of these designs is completely satisfactory for a variety of reasons noted herein.

One challenge in chemical gradient assays is to maintain a constant fluid flow to ensure that the movement of cells is a result of chemotaxis behavior and not as a result of variations in the flow field. A non-steady flow will also limit the time bacteria are exposed to the gradient, allowing the cells to exit the channel with the flow instead of responding to chemoeffectors. In addition, the flow creates a small drag force on the cells. See, e.g., Walker G M, et al., *Lab on a Chip* 2005, 5(6):611-618. Another challenge is to create a uniform chemical gradient across the channel over the experimental period.

The present disclosure provides assay methods, devices, and kits for bacterial analysis, such as chemotaxis evaluation, based on porous membrane microfabrication and microfluidic techniques.

Though chemotaxis-specific methods and devices are specifically exemplified in the present disclosure, it is not intended to be so limited. In particular, the inventors have determined that other stimuli, in addition to or in lieu of, can be utilized to identify or separate live cells in a sample that often comprises a mixed population of live and dead cells (e.g., bacterial cells contemplated herein such as *E. coli.*). Certain of these stimuli include the use of an electric field, and/or the use of a temperature gradient to induce a specific movement of a cell of interest toward or away from the stimuli. For example, in certain embodiments, a microelectrode is provided adjacent to a sample channel that provides an electric field gradient extending into the sample channel or a chamber. Within this electric field gradient, live cells move toward an increasing positive electric field strength (i.e., toward a cathode), thus separating from dead cells.

In another embodiment, a temperature gradient is provided extending into the sample channel or chamber. The temperature gradient has an area of temperature approaching, at, or exceeding room temperature (e.g., 37° C.) at its apex. In one embodiment, within a temperature gradient, live cells move toward an increasing temperature, or toward room temperature, from a colder environment, thus separating from dead cells. In another embodiment, within a temperature gradient, live cells move toward a decreasing temperature as it approaches room temperature, from a hotter environment, thus separating from dead cells. Multi-laminar flow device designs or chambered device designs (as described herein) may be used in such embodiments.

Example 1

In one exemplary embodiment, a three-channel, six-chamber device provides static fluid flow, thereby eliminating hydrodynamic influences on the motility of the cell under evaluation or cells in a sample, and establishing a linear chemical gradient across all chambers. In certain frequent embodiments, a syringe pump is unnecessary to achieve the microfluidic analyses described herein. Also often, clean room processing is unnecessary for chemotaxis evaluation of a cell or sample. The inventors have discovered that these aspects dramatically reduce system complexities and cost. The inventors have also discovered that the lower cost, simplicity of handling, and ability for direct observations make the presently provided designs useful for the study of cell behaviors under the influence of different chemical gradients.

Materials and Methods

Fluorescein, phosphate buffer saline (PBS), Luria-Bertani Broth medium (LB), Tris buffer saline (Tris), L-aspartic acid, nickel chloride were purchased from Sigma Aldrich (St Louis, Mo.). PBS, Tris and LB were autoclaved before use. *E Coli* strain (ATCC 43888) was obtained from Fisher Scientific (Pittsburgh, Pa.). All cultures were grown in 10 mL of LB incubated at 37° C. for approximately 4 hours until the optical density of sample at wavelength of 600 nm reached 0.8. Optical density at 600 nm was measured for cell culture quantification.

Agilent UV-Visible spectrometer (Agilent 8453) was used for optical density measurement. Nikon Ti fluorescence microscope was used to measure the fluorescence intensity and cell tracking Images were acquired and analyzed by Nikon NIS Element and MATLAB software.

Fabrication Process of Microfluidic Device

An exemplary device described and depicted herein consists of a center channel that delivers a bacteria sample from a small reservoir to the central interaction region, where the channel is perpendicularly connected to six chambers. As shown in FIG. 1, two additional channels are provided parallel to the center channel located on each side. These channels serve as a source for generating a chemical gradient in the chambers. A nitrocellulose membrane (Millipore type GSTF) with a 0.22 μm pore size serves as a porous medium that separates the side channels from the chambers while allowing chemicals to diffuse through to the chambers. The pore size of 0.22 μm was selected as an exemplary pore size to ensure chemical axial flow through the porous nitrocellulose substrate, while prohibiting the passage of the cells or analyte to be analyzed through the porous substrate.

Other pore sizes may be utilized depending on the type of assay and cells or analyte to be analyzed are contemplated herein.

The channels of the exemplary device were fabricated from the nitrocellulose membrane using a rapid prototyping technique. Briefly, a CAD layout of the geometry was created in AutoCAD and was transferred to a laser cutting tool (Trotec, model speedy 300 engraver equipped with a SYNRAD series f100 laser tube). The laser cutter focuses a high power laser beam into a very tiny point; material is dislodged from the surface of a substrate upon exposure to this point. The laser head was placed on a robotic arm that was controlled based on the input CAD layout. First, the membranes were cut into pieces about the size of a microscope slide and placed on the laser cutter stage. Dry membranes are fragile; therefore membranes were soaked in deionized water before the cutting operation. Other fabrication techniques to produce devices having the desired attributes are contemplated herein.

Figure 2:
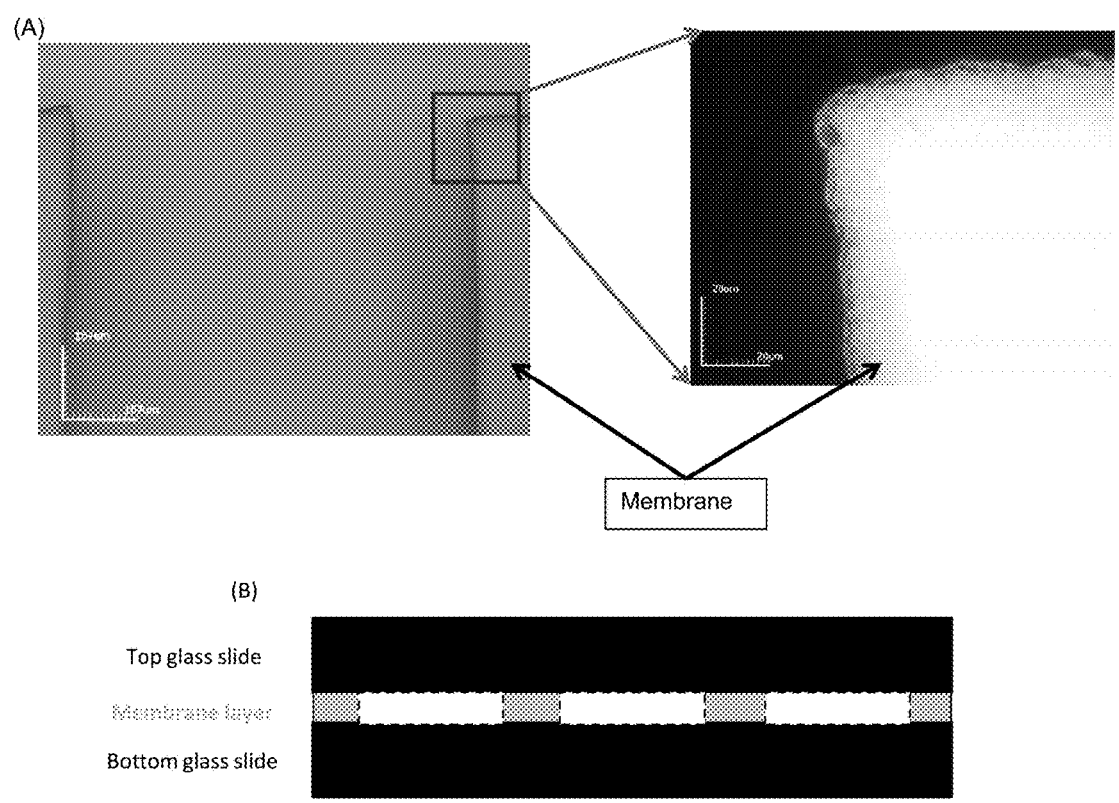
FIG. 2 (*a*) depicts a microscopic pictures of an exemplary microfluidic channel with an enlarged view of the edge of the membrane; (b) side view of an exemplary microfluidic porous substrate sandwiched between two glass slides.
Figure 3:
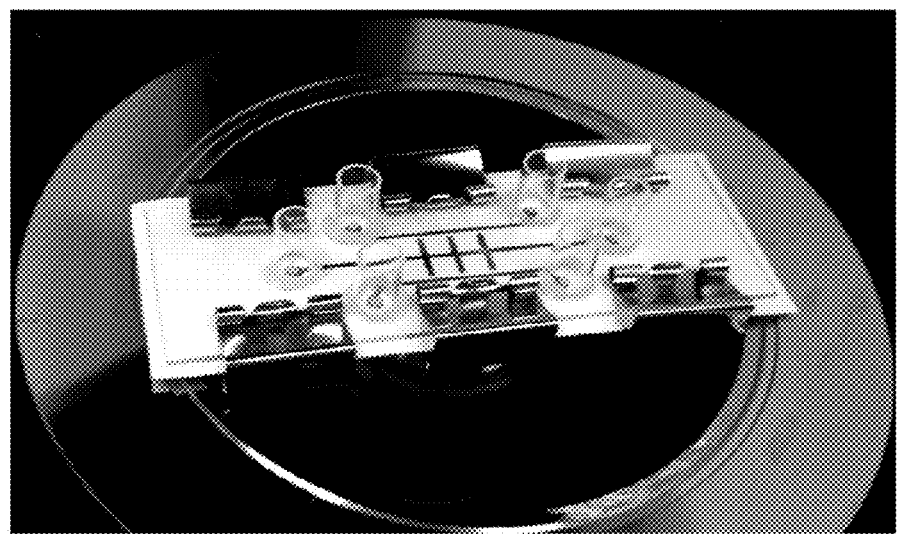
FIG. 3 depicts examples of final assemblies of an exemplary microfluidic devices.
Figure 3:

The microfluidic design was fabricated on the membrane by utilizing 18 W of laser power while the laser head scanning speed was set to 35 mm/s. The edges of the membrane cut by laser are smooth and sharp as shown, for example, in FIG. 2A. The resulting thin layout was sandwiched between two pre-cleaned glass microscope slides as shown in FIG. 2B. The assembly was held together by six small clips, a picture of the final microfluidic device is shown in FIG. 3. Other means of holding the slides in place are contemplated, including the use of adhesive, hydrodynamic forces (e.g., between the two slides), or other fastening means. The slides were 25×75 mm wide and 1 mm thick. In addition to their wide availability, microscope glass slides allow the device to be compatible with microscope platforms for flow and cell observations.

Inlet and outlet ports (6 in total) were made on the top slide by means of a laser cutter machine; 60% of the maximum laser power was utilized for engraving the holes in the glass, multiple passes of the laser beam were required to make a hole. Six small cylindrical pieces (5 mm in diameter, 8 mm in length) were cut from a glass tube and glued (Loctite E-120HP) above the ports to serve as small fluid reservoirs of about 150 µl capacity. The thickness of the membrane layer was 120 µm, which defines the height of the channels and chambers.

Experimental Setup

After 4 hours incubation at 37° C., 3 ml of the cell culture were taken into a syringe and passed through a 0.22 µm syringe filter (Thermo Scientific) for buffer exchange. The same volume of buffer saline was taken back through the filter into the syringe; suspending the cells in the buffer saline medium. This process was repeated three times to ensure the complete exchange of growth medium with buffer saline. The bacterial motility was not affected. The conventional centrifugation method of medium exchange was evaluated for use in this work, however it was observed that the bacteria motility was reduced significantly and thus produced a smaller percent yield.

The microfluidic device was prepared as follow. The top glass assembly was properly cleaned and reused for many experiments, while the membrane and the bottom glass were renewed for each experiment. Acetone, isopropanol, and DI water were used to effectively clean the top glass and reservoirs. The membrane layer was soaked entirely in buffer solution for 30 min before use to ensure the removal of all air bubbles. The soaked membrane was then aligned with the inlet/outlet ports on the top glass and sandwiched between the top glass and another glass slide using 6 small stainless steel clips that provide constant and consistent pressure over the entire membrane area, as shown in FIG. 3.

After the device assembly, the input reservoirs were filled with buffer and the output reservoirs were vacuumed for a few seconds, the strong resulting flow expels all possible bubbles from the microfluidic system. The channels were inspected under microscope before conducting tests. All the experiments were conducted at least for three times to determine reproducibility. The bacterial chemotaxis experiments were conducted at an ambient temperature of 36° C.

Results

It was important to test the establishment of the chemical gradient inside the microfluidic chambers before the chemotaxis studies. The distribution of fluorescent dye in the chambers was measured using a fluorescence microscope to simulate the concentration gradient profile of the chemoeffectors. The intensity of fluorescence emission from a fluorescein solution is proportional to its concentration for concentrations less than 0.1 mM. Therefore, although it is challenging to determine the actual concentration field of a certain chemoeffector in the microfluidic device, using the fluorescence dye under the same experimental conditions, it was possible to obtain information about the establishment rate of the concentration gradient as their diffusion coefficients are similar. See, e.g., Jeon H, et al., *Biomed Microdevices* 2009, 11(5):1135-1143.

For this fluorescence intensity measurement, one of the side channels was filled with 0.1 mM fluorescein sodium salt solution in the PBS buffer and the other two channels (center channel and the other side channel) were filled with plain PBS buffer. The inverted Nikon Ti microscope was used to obtain the fluorescence intensity inside the chamber. Both excitation and emitted lights were filtered through a Nikon FITC filter set. Excitation light was collected through a 10× Plan Fluor objective and redirected to the sensitive Hamamatsu camera.

Figure 4:
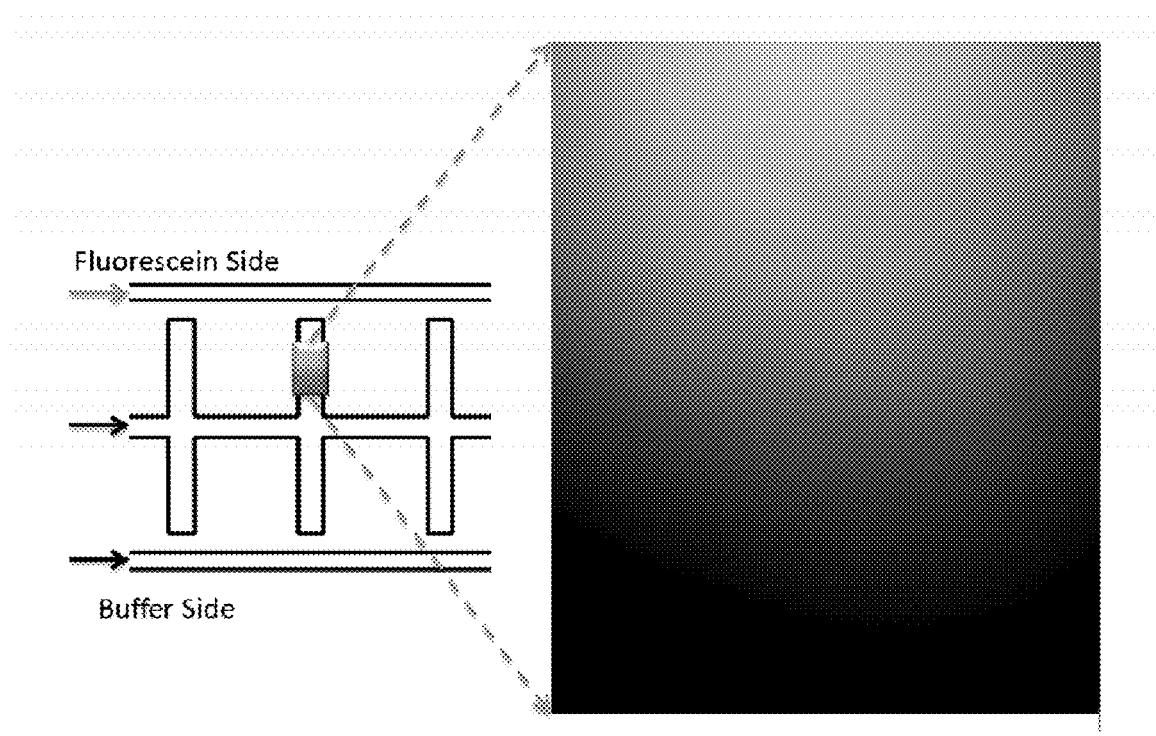
FIG. 4 depicts a fluorescence image obtained from the center chamber of an exemplary microfluidic device showing a stable concentration gradient 30 min after flow of chemoeffectors started in the side channel.
Figure 5:
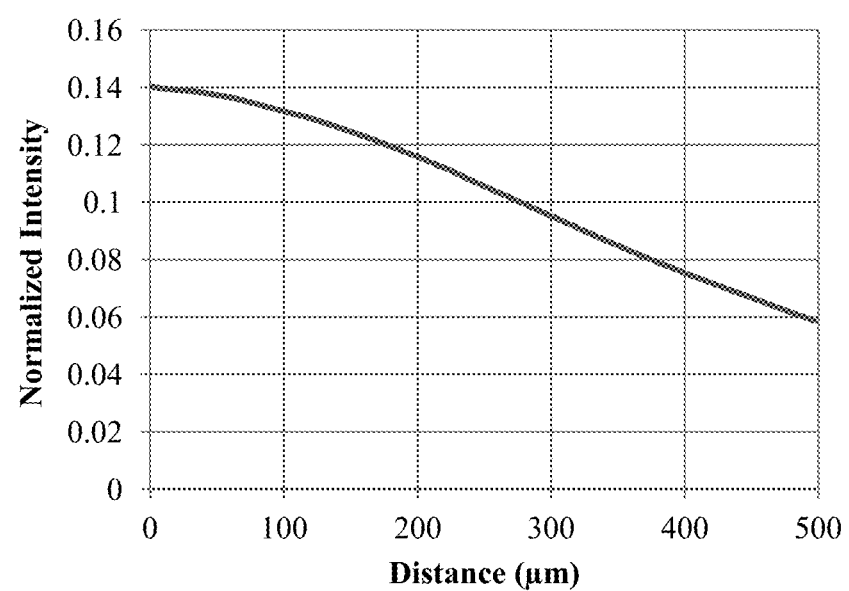
FIG. 5 depicts an intensity profile normalized by the intensity in fluorescein channel corresponding to FIG. 4. The x-axis represents the distance from the end of the chamber.

It was observed that fluorescein concentration levels in the chamber reached a detectable level within 4 minutes after starting the flow. However the chemical gradient presented only in a small region at the end of the chambers close to the source channel and no detectable dye concentration was found in the regions close to center channel. As time passed, the dye molecules continue to diffuse from source channel into the chambers, raising the chemical concentration levels in the chambers. After 20 min, the chemical gradient was clearly established throughout the length of each chambers. FIG. 4 shows the fluorescence intensity variation in the chamber after 30 min of starting the flow. By this time a quasi-linear concentration gradient was established in the chamber. The corresponding intensity profile across the chamber is presented in FIG. 5, the intensity values are normalized by the intensity of fluorescence dye in the source channel. Maximum fluorescein concentration in the chamber did not exceed 20% of the concentration in the fluorescein source channel. As long as the flows are maintained in the three channels, this concentration gradient remained steady for an additional 30 min of observations. When measurement parameters of the device materials, porous substrate types or pore sizes, channels and/or chambers, and/or test chemicals (e.g., chemoattractants or chemorepellents) are altered from the exemplary device, a fluorescent assay is conducted to verify timing and extent of the chemical gradient.

Chemotactic response of cells to a chemical gradient was tested in another set of experiments. For these experiments *E. Coli* cells were prepared with the procedure described before and suspended in buffer. $OD_{600}$ of the cell solution was adjusted to 0.35 for all experiments to have a consistent total population of bacteria. While the buffer is still running in all channels, the center reservoir was filled with the bacteria sample and the other two side reservoirs of the exemplary device were filled with the corresponding buffer or chemo-attractant/repellent. The exemplary microfluidic device was placed on a Nikon Eclipse Ti microscope and observations were performed via a 10× phase contrast objective lens. Images were captured by a digital camera (Hamamatsu ORCa-Flash2.8) mounted on the microscope and controlled by Nikon NIS Elements software on the PC.

Figure 6:
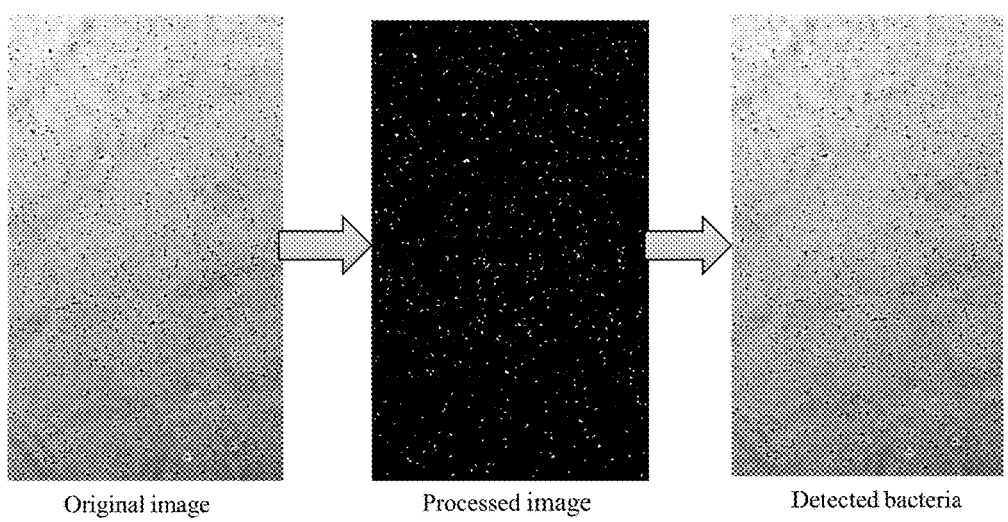
FIG. 6 depicts an exemplary image processing procedure applied on an image of bacteria in the microfluidic chamber.

The resulting images contain a large number of cells therefore an automatic image processing code was developed in MATLAB environment to carry out the cell population analysis. As shown in FIG. 6, images were digitally processed with a spatial filter that removes high frequency noise and only keeps features in the image that are close to the size of the cells. Further image processing intensity analysis of the resulting image recognizes the cells and their corresponding location in the field of view based on the identification of intensity peaks.

Figure 7:
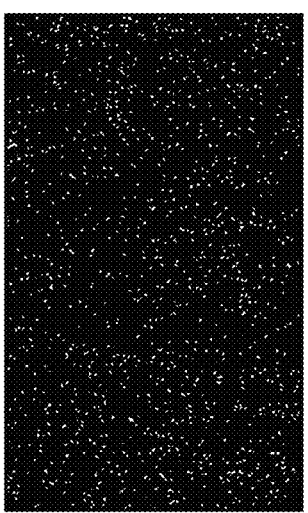
FIG. 7 depicts exemplary images of bacteria in the center chamber of an exemplary device (the exemplary device having three channels, and three chambers on each side of the center channel, e.g., as in the device of FIG. 1 or FIG. 3) for three different assays: (a) 0.5 mM L-aspartic acid solution used as attractant; (b) 0.5 mM $NiCl_2$ used as repellent; and (c) a control assay with PBS buffer in both of the side channels.
Figure 7:
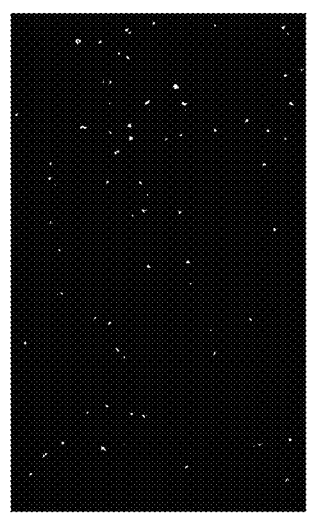
Figure 7:
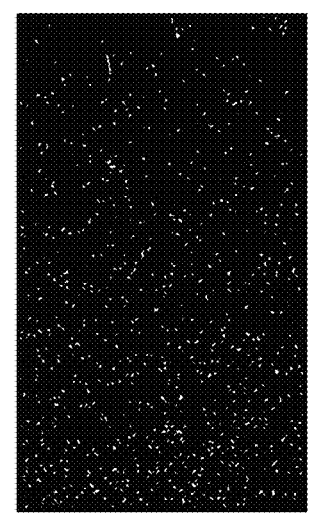
Figure 7:
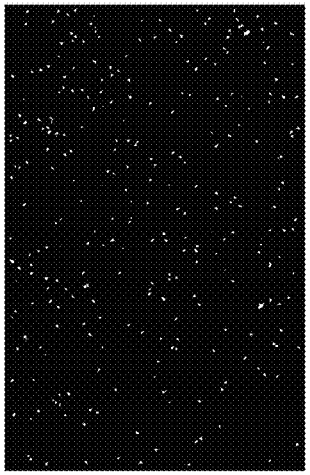
Figure 7:
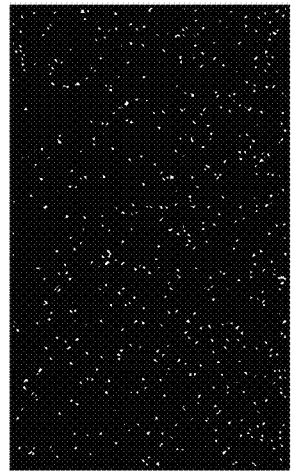
Figure 7:
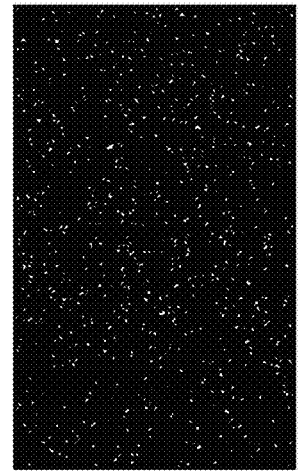
Figure 8:
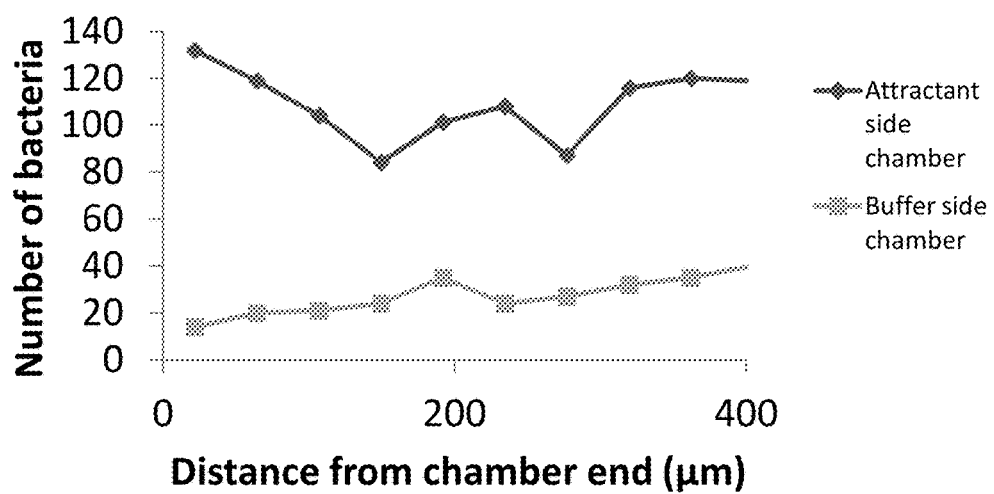
FIG. 8 depicts bacteria distribution along a length of the center chamber in an exemplary device (e.g., as in the device of FIG. 1 or FIG. 3) for (a) an assay where 0.5 mM L-aspartic acid solution in PBS buffer were used as attractant while PBS buffer was used on the opposite side channel.

For a chemo-attractant study, 0.5 mM L-aspartic acid potassium salt solution in PBS buffer was used as the attractant. By running this solution in a side channel, the maximum concentration of attractant in the adjacent chambers can reach about 0.1 mM based on the results of fluorescence measurement experiment. PBS buffer was run in the other side channel while the *E. Coli* sample prepared in PBS buffer was injected into the center channel. As bacteria reached the entrance of the chambers it was observed that more bacteria moved into the chambers on the attractant side. FIG. 7a shows images of chambers located on attractant side and buffer side after about 30 min of loading the sample and liquids into the microfluidic device. Spatial histograms of the bacteria distribution along the chambers were obtained using our image processing method and are plotted in FIGS. 8-10.

The strength of chemotaxis can be quantified using chemotactic index $I_C$, which measures the magnitude of the accumulation of a population within a certain region, relative to background levels. See, e.g., Ahmed T, S et al., *Integrative Biology* 2010, 2(11-12):604-629. $I_C=1$ corresponds to a uniform cell distribution (no chemotaxis), while strong chemotaxis is characterized by larger values of $I_C$. See, e.g., Seymour J R, et al., *Journal of Plankton Research* 2009, 31(12):1557-1561. The chemotaxis index of 0.5 mM aspartic acid was calculated to be 4, which means the total number of cells in the attractant chambers was 4 times as big as the number of cells in the buffer side chambers.

Figure 9:
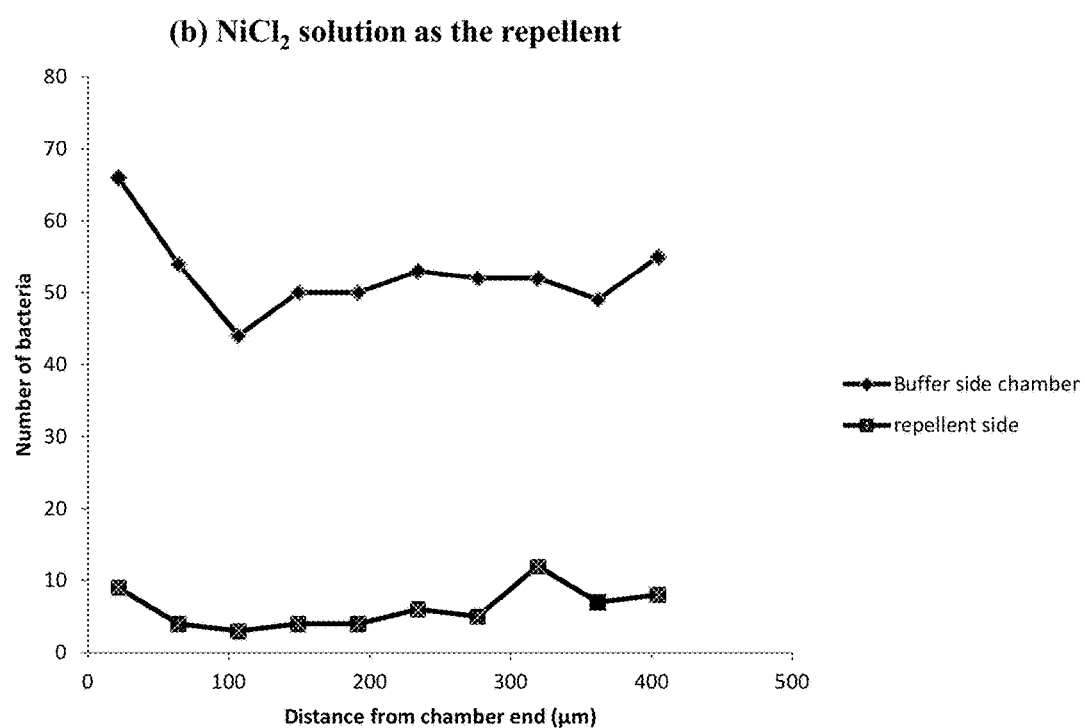
FIG. 9 depicts bacteria distribution along a length of the center chamber in an exemplary device (e.g., as in the device of FIG. 1 or FIG. 3) for an assay where 0.5 mM $NiCl_2$ solution in PBS buffer were used as repellent while PBS buffer was used on the opposite side channel.
Figure 10:
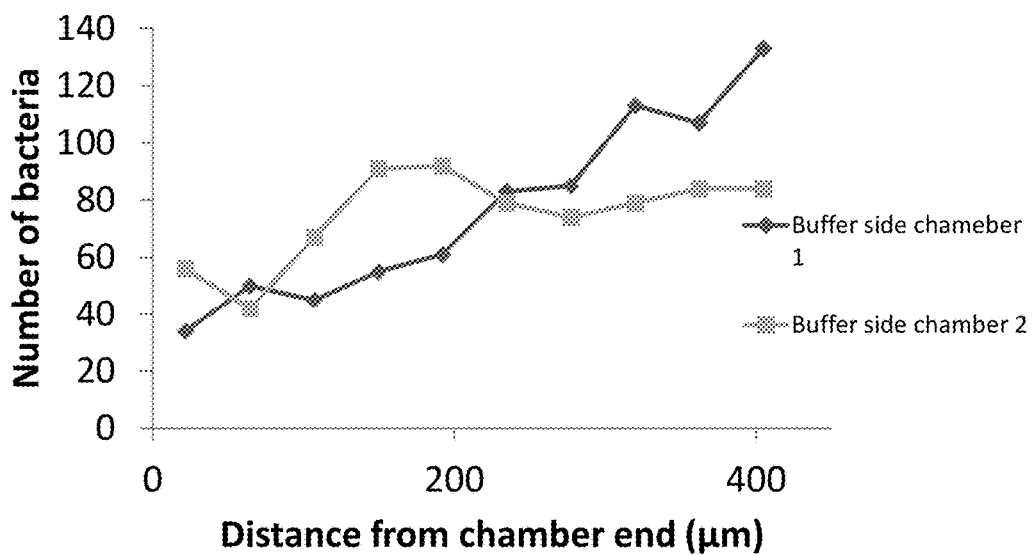
FIG. 10 depicts bacteria distribution along the length of a center chamber in an exemplary device (e.g., as in the device of FIG. 1 or FIG. 3) for a control assay where PBS buffer was run in both side channels.

In the next set of experiments, a solution of 0.5 mM $NiCl_2$ was used as a repellent for *E Coli*. The same steps as the attractant experiment were followed, however because nickel ions precipitate in PBS buffer, Tris Buffered Saline (TBS) was used as the bacteria sample medium and the carrier fluid. As it can be seen in from FIGS. 7 and 8, the chemotaxis effect is more pronounced in this experiment and the ratio of bacteria count in the buffer chambers is more than 8 times bigger than bacteria count in the repellent side chambers. The corresponding quantified results are shown in FIG. 9.

The control experiment was carried out by keeping all the details of the chemo-attractant/repellent experiment the same, except that solely PBS buffer was used in both side channels; therefore there was no chemical gradient in the chambers. c shows images of bacteria in two opposite chambers after 30 min of starting the flow. The number of bacteria in those chambers were calculated and compared in FIG. 10. The ratio of bacteria population in the two chambers is 1.02 which shows no significant difference across the opposite chambers for the control experiment. This confirms no other phenomena other than chemotaxis, e.g. fluid dynamics, have contributed to the uneven bacteria distribution in opposite chambers for the chemo-attractant/-repellent experiments.

DISCUSSION

In this example an design of an exemplary porous membrane based microfluidic device is provided, and used to study bacterial chemotaxis in a model system. One exemplary device consists of three parallel channels, and sets of chambers connected perpendicularly to each side of the center channel (see FIG. 3). This design provides a flow-free environment in chambers for bacterial to sense the gradient of the chemoeffectors and make a biased shift without the interference from the bulk flow. The exemplary microfluidic devices described herein exploit cell movement to separate live cells from dead ones, for example, for real-time pathogen detection. Though not wishing to be bound by any particular theory, by changing the local environment of the cells, their movement can be manipulated so all the viable cells can, for example, be separated and concentrated. The bacteria interact with the chemical stimulus in the center channel and then move based on the nature of these interactions, either toward it if it is a food source or away if it is a repellant. The separated bacteria are then collected (e.g., collect via cellular movement rather than via current flow) in the channel's respective outlets or chambers.

The linear chemical gradient of chemoeffectors inside each chamber can be established in minutes after the chemicals were introduced the system by diffusing a chemical through a porous membrane located in the sidewall of the chambers. This is consistent with a report for chemical diffusion through a nitrocellulose membrane. Diao J, et al., *Lab on a Chip* 2006, 6(3):381-388. In addition, the stability of the chemical gradient the exemplified designs is independent of the current(s) in the source and/or sink channels, which is a great advantage compared to the designs using multiple laminar flows to establish chemical gradients.

In one example, the chemoeffector is injected into the device through a side channel (including multiple side channels). Since there is a gap (e.g., of about 0.6 mm) between the side channel and chamber (including multiple chambers), the chemoeffector's only mode of transport to the chamber (including multiple chambers) is diffusion through the porous nitrocellulose substrate via axial flow. The gap length between the side channel and the chamber may vary. When a chemical solution (or a fluid containing a chemoeffector) is fed into a side channel, chemical molecules diffuse across the nitrocellulose membrane into the chamber until a stable linear chemical concentration gradient is established. This steady state linear concentration is explained by:

$$C_2/C_1=1+(D_1 \cdot L/D_2 \cdot l)$$

where $C_2$ is the chemical concentration in the source channel, $C_1$ is the chemical concentration at the end of the chamber, $D_1$ is the diffusion coefficient through the chamber, $D_2$ is the diffusion coefficient through the nitrocellulose membrane, L is the length of the membrane/gap between the side channel and chamber, and l is the length of the chamber.

Figure 11:
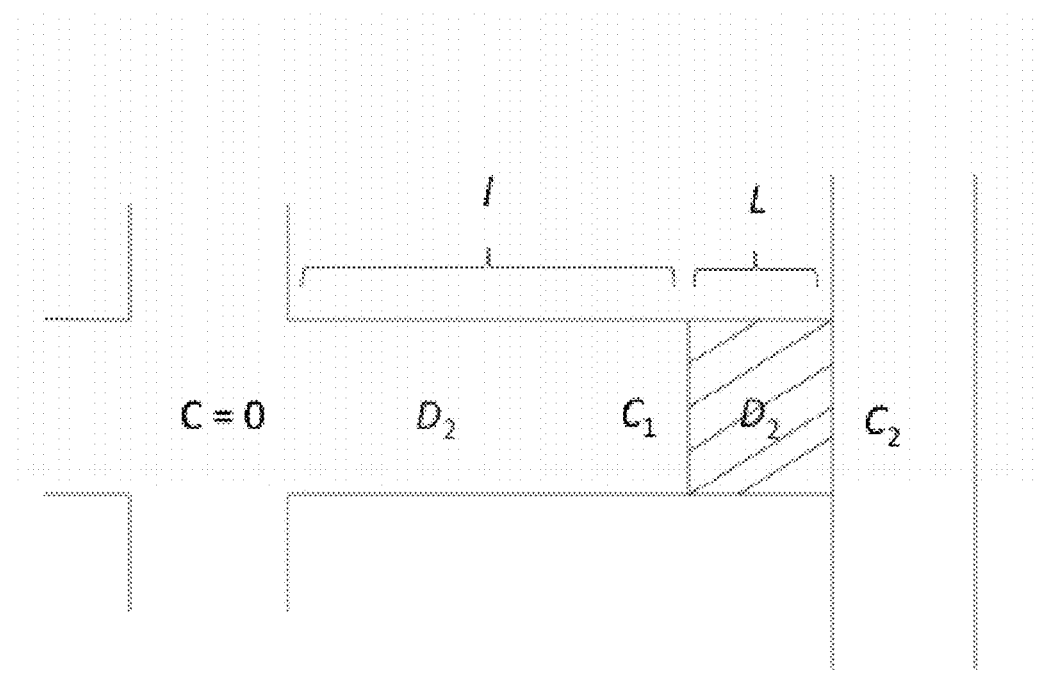
FIG. 11 depicts exemplary components and measurement parameters involved in devising and generating an exemplary linear chemical gradient.

FIG. 11 shows the labeled components involved in generating a linear concentration gradient. By changing the lengths of L and l, the concentration gradient in the chamber can be varied. For example, the gaps between the chambers and the source channel are often adjusted so the concentration effect of the chemoeffectors can be studied simultaneously in the same device.

Through fluorescence microscopy of the dissolved dye it was found that, after 20 minutes, a linear concentration gradient is established. The rate of establishing a linear concentration gradient and the maximum chemical concentration inside the chambers are dependent, for example, on the membrane pore size as well as the gap size between the side channel and the chambers. Inone exemplary device the nitrocellulose membrane had a pore size of 0.22 µm so that it will solely permit molecular diffusion and prohibit cell passage, while the gap is 600 µm. Adjusting these variables is within the scope of the present disclosure and would alter the rate of diffusion across the membrane thus modifying the concentration of chemicals found inside the chamber(s).

To study the chemotaxis response, bacteria cells at logarithmic phase were typically used as the bacteria are more motile and more strongly chemotactic than in stationary phase. See, e.g., Staropoli J F, Alon U, *Biophysical Journal* 2000, 78(1):513-519. Therefore, the bacterial cells were harvested after 4 hours incubation at 37° C. After a careful buffer exchange to minimize the damages on flagella, the motility of the cells was inspected under the microscope. The cells were very motile. Some of the cells can reach the end of chamber in less than 3 minutes with a swimming speed greater than 27 µm/sec, which is in agreement with the reported averaged speed of 14 to 30 µm/s for *E Coli* cells. Se, e.g., Liu Z, Papadopoulo K D, *Biotechnology and Bioengineering* 1996, 51:120-125; Martinez Vincent A, et al., *Biophysical Journal* 2012, 103(8):1637-1647.

The optimum concentration levels of aspartic acid as an exemplary chemo-attractant for chemotaxis experiments vary depending on the assays and designs of the microfluidic devices. The peak concentration for a capillary based chemotaxis assay is about 10 mM. See, e.g., Mesibov R, Adler J, *Journal of Bacteriology* 1972, 112(1):315-326. In a three-channel microfluidic setup using the agarose gel as the diffusive medium, 0.5 mM was reported to generate the maximum chemotactic response for *E Coli*. See, e.g., Diao J, et al., *Lab on a Chip* 2006, 6(3):381-388. While, for a plug assay chemotaxis study, it was reported to have 1.74 chemotactic index (peak response) for about 20 mM aspartic acid on *E Coli*. We have also tried different aspartic acid concentrations and realized that a more significant chemotactic response was obtained when 0.5 mM was used. The pronounced chemotactic response at much lower concentration of the aspartic acid in the microfluidic devices compared to capillary and/or plug based assays indicate the enhanced and unexpected sensitivity of the presently described microfluidic based chemotaxis assays.

After introducing the repellent $Ni^{2+}$, it was observed the motility of the cells were reduced to some degree due to an increase in tumbling frequency. Although at higher concentrations, $Ni^{2+}$ decreased the membrane fluidity, those concentrations are much higher than the level we used to elicit a repellent response. See, e.g., Eisenbach M, et al., *Journal of Bacteriology* 1990, 172(9):5218-5224. The concentration of $Ni^{2+}$ as the chemorepellent for *E. Coli* is, for example, typically from 0.1 mM to 10 mM. It has been reported that the electrostatic absorption between the negative charged organic acid on the cell surface to the positive charged $Ni^{2+}$ is directly related to the chemotactic response. See, e.g., Borrok D, et al., *Environmental Science & Technology* 2005, 39(14):5227-5233. Higher chemotactic response were obtained when the surface absorption of $Ni^{2+}$ was higher.

The combination of a flexible design process and rapid fabrication techniques using different types of the nitrocellulose membrane make it possible to change the geometry of channels and chambers resulting in a range of chemical gradient profiles by setting different gap sizes for the chambers on a single device. In addition, bacterial cells response to different chemical environments can be examined simultaneously by comparing, for example, two opposing chambers; while the redundancy of additional sets of chambers (when 4 or more chambers are provided, for example) allow for repeatability and consistency analysis.

Using a rapid prototyping technique described herein, making device changes is permitted by modification of the input CAD for membrane channel/chamber layout. However the height of the channels is limited by the thickness of the porous substrate (membrane) layer. Should a custom height be applied for which a commercial membrane doesn't exist, an alternative fabrication method can be employed to achieve a similar three-channel design. For example, the channels may be etched in a glass slide or a PDMS layer (as a fluid impermeable layer), and a porous substrate/membrane placed between the two solid fluid impermeable layers. In such an orientation, the membrane would form the top of bottom of the channels. In such an embodiment, fluid containing a chemoeffector would, similarly, diffuse through the porous medium from a side channel to a chamber. The direction of the axial flow would be similar, though the chemoeffector would (e.g., if the porous substrate comprised the top of the channel) pass up from the side channel into the porous substrate and across the porous substrate to a chamber where the chemoeffector would diffuse down into the fluid in the chamber to create a linear chemical gradient. The quality of the geometry obtained from an exemplary etching process may be preferred over those obtained from laser cutting of a porous substrate, and such a system could be more compatible with other microfluidic applications (i.e., integration a mixer in the flow). However, since the membrane is continuous, the optical pathway through the channel may be lost and therefore bright field microscopy may not be applied for observations unless windows or optically transparent portions were provided in the membrane. Alternatively or in addition, fluorescence microscopy may be used if the membrane does not show an auto-fluorescence property.

In this example, we designed, fabricated and tested a three-channel microfluidic device that has been shown to be useful for generating a linear concentration gradient and for the study of bacterial chemotaxis. The exemplary device is composed of a 120 µm nitrocellulose membrane sandwiched between two glass slides. The microfluidic channels were patterned on the membrane layer by means of a precise laser cutter tool; this eliminated the need for cleanroom processes and dramatically reduced the final cost of the product.

The successful establishment of a linear chemical gradient was tested using fluorescence dye and fluorescence microscopy. These results showed that the concentration gradient starts to develop immediately after injecting chemoeffectors, and that after 20 minutes a linear gradient was established across all chambers. The described devices were able to produce a linear chemical gradient across the chambers, where cells are free of flow disturbances. This results in cell movement caused solely by cellular motility and chemotactic behavior opposed to by fluid flow. Chemotaxis assays were conducted using *Escherichia coli* as an exemplary analyte and the exemplary chemoeffectors 500 µm L-aspartic acid in buffer solution and 500 µm $NiCl_2$ in buffer solution (the chemoattractant and a chemorepellent, respectively). Results of image processing show that after 20 minutes in both scenarios a significant response to the chemoeffectors by the E. coli cells was observed.

The exemplary microfluidic devices provide the accurate and sensitive evaluation of any chemotactic bacteria in addition to E. coli. Excellent optical access to the sample in the present devices permits motility quantification and time analysis of bacterial movement. Lower cost, simplicity of handling, and ability for direct observations make this design useful for study of cell behaviors under influence of different chemical gradients.

In sum, an exemplary three-channel microfluidic device is provided with embedded chambers useful for the study of bacterial chemotaxis and sample processing. The device is capable of generating linear chemical gradients in the embedded chambers that are free of flow disturbances. These linear chemical gradients are established by diffusing a chemical through widely available nitrocellulose material that serves as a permeable membrane between the adjacent supply channels and embedded chambers. The generated gradients were confirmed by measuring the fluorescent molecules diffused through the source channel into the chamber on a fluorescence microscope. As the gradients were generated without through-flow, cell movement in the chambers was caused by the cells' random motility or chemotactic response up or down a chemical gradient and not interfered by fluid flow. The advantages of this microfluidic design include (i) a rapid implementation of a static chemical gradient can be established; (ii) two chemoeffectors can be simultaneously studied and compared; (iii) multiple chambers can be used for a reproducible study; (iv) the design can be fabricated at a low cost. Using a Nikon Ti microscope, food borne pathogen E Coli 0157 was observed in the microfluidic device to swim towards the attractant, L-aspartic acid (500 uM) and away from the repellent, $NiCl_2$ (500 uM). The chemotactic responses to the chemicals were quantified using the cell population ratios in the chambers close to the source channel and the buffer channel respectively.

Example 2

Another novel way to separate viable cells from dead cells based on bacterial taxis capabilities is explored in this example. Bacteria can sense nutrients such as sugars or organic acids and move towards them—a process is known as chemotaxis. See, e.g., Celani, A. and M. Vergassola, PNAS, 2010. 107(4): p. 1391-1396; Miller, L. D., et al., Chapter 3 *Diversity in Bacterial Chemotactic Responses and Niche Adaptation, in Advances in Applied Microbiology*, S. S. Allen I. Laskin and M. G. Geoffrey, Editors. 2009, Academic Press. p. 53-75. Additionally, bacteria can also move away from harmful substances such as waste products and in response to temperature, electric fields, gravity, etc. By changing the local environment of the cells using a unique microfluidic design, live cells can be separated. This Example provides an exemplary microfluidic system, which provides separation efficiency and throughput volume that has not been possible to date by testing the effects of changes in flow speed, attractant and repellent concentration and detergent. The advantages of porous substrates, as described herein, allow for rapid production and implementation of an assay by the establishment of a chemical gradients.

Methods and Materials

Preparation of the Samples:

Fluorescein, Luria-Bertani Broth medium (LB), Tris buffer saline, L-aspartic acid, nickel chloride were purchased from Sigma-Aldrich (St. Louis, Mo.). Tris and LB were autoclaved before use. E. coli (ATCC 43888) was obtained from Fisher Scientific (Pittsburgh, Pa.). All cultures were grown in 10 ml of LB and incubated for approximately 3 hours. The cell culture was then taken into a syringe and passed through a 0.22 um syringe filter (Thermo Scientific) for buffer exchange from LB to Tris. The process was repeated three times. The OD of the solution was then tested using Agilent UV-Visible spectrometer (Agilent 8453). Tests were run using an OD between 0.2 and 0.3 at 600 nm. The chemotactic attractants and repellents were created at various concentrations ranging between 5 mmol and 20 mmol in Tris buffer.

Fabrication of the Microfluidic Device and Setup:

The device consists of a center channel flanked with Y-shaped import and export channels. The center channel is parallel to two exterior channels on each side. These outer channels serve to create a chemical gradient within the center channel. The channels of the device were cut into a nitrocellulose membrane (Millipore type GSTF) with a pore size of 0.22 um using a laser cutting tool (Trotec, model speedy 300 engraver equipped with a SYNRAD series f100 laser tube). The channel layout was first created using AutoCAD, the design was then plotted onto the membranes using the laser cutter. Using a small lens (focal length −38.1 mm; nominal cut width—25 um) the porous substrate (membrane) was precisely cut with the laser to create channels. Because the membrane is fragile, it was first wetted with deionized water before cutting. The thickness of the channels was determined by the thickness of the membranes at about 120 μm. Each membrane was provided for single use.

For each assay a new membrane was soaked in a Tris buffer and then sandwiched between two pre-cleaned glass microscope slides. After assembly, reservoirs and channels were flushed with buffer to clear any air bubbles or debris using a vacuum pump. Silicone tubes were attached to the device over inlet and outlet ports of the device. before mounting to the stage of an inverted Nikon Ti microscope. The tubes were then connected to a 1 ml leur-lok syringe via a needle (BD PrecisionGlide Needle). These needles rested in a KD Scientific Syringe pump 200 series set on withdrawal.

Attractant (Aspartic Acid) was injected into the reservoir at the entrance of the bottom channel. The repellent (Nickle (ii)) chloride was placed in the reservoir at the entrance of the top channel. These chemicals were then given approximately 20 minutes to flow through the membrane creating a concentration gradient in the center channel. Finally, bacteria and Tris buffer were introduced to the central channel via two inlets simultaneously. Videos were taken every 10 minutes for 40 minutes at the beginning, middle and end of the middle channel using a Nikon NIS Element. These videos were then processed and analyzed using NIS Elements, MATLAB and Image-J. The level of separation was also measured by plate cultures.

Results

Figure 12:
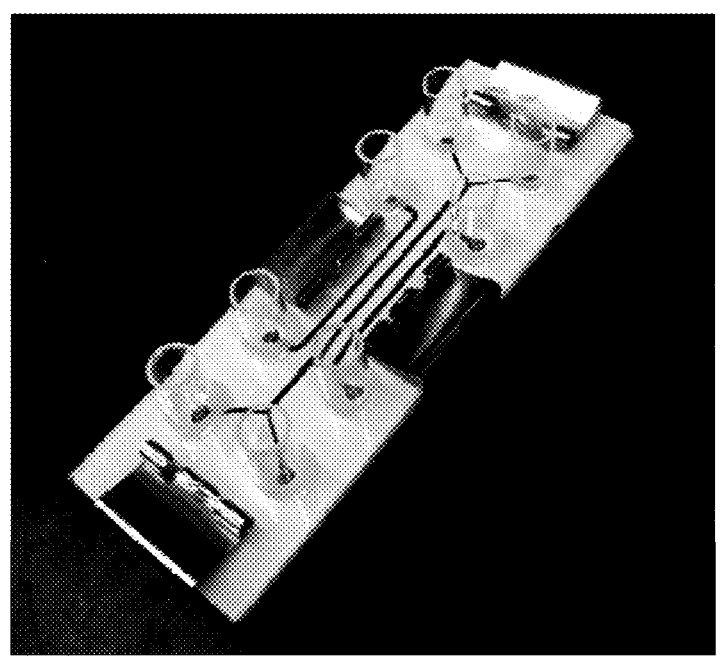
FIG. 12 depicts (A) a picture an exemplary device; and a depiction of (B) another exemplary channel arrangement and orientation within a porous substrate membrane.
Figure 12:
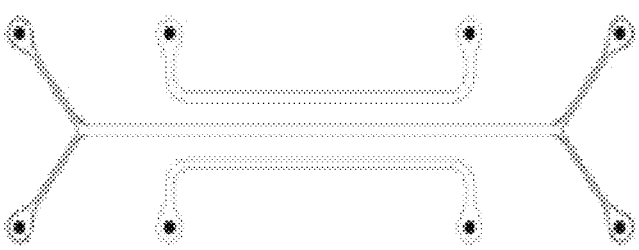

Example 1 demonstrates viable separation capabilities via chemotaxis and cell motility. In certain embodiments of this Example, however, the separated cells are trapped inside the chambers. In order to obtain the separated cells, a dual-flow microfluidic design and device was developed. The newly designed microfluidic system is based on the laminar flow property in microfluidic channels. Fluids moving in μm-scale channels have properties that often do not exist on the macroscopic scale. For example, flow inside a micro channel is laminar, with Reynolds' numbers of 1 or less. Thus, when multiple adjacent liquid streams run in parallel (i.e., flow next to each other) on this scale the only mixing that occurs is by molecular diffusion. The exemplary microfluidic device described herein contains three flow channels. The two side channels are used to deliver chemical attractants and repellents. The center channel will have two inlets, one for sample and one for buffer, which converge into a single center channel at the entrance (upstream) and then split into 2 collection chambers at the exit (downstream) with individual downstream collection outlets as shown in FIGS. 12 (A & B).

The chemoeffectors provided in the side channels reach inside the central channel by diffusing through the nitrocellulose membrane. Dead bacteria, being unable to exhibit chemotactic responses, generally stay in the primary sample stream and exit the channel in the corresponding collection outlets. For example, referring to FIG. 12B, if the inlet for the sample stream containing cells is the top left inlet of the central channel (the buffer inlet being on the bottom left), then dead cells would pass through to the top right outlet of the central channel. Cells eliciting a desired chemotactic response that brings them into the buffer channel from the sample channel will end in the bottom right outlet of the central channel. The responsive and viable bacteria sense the chemicals (combination of pulling and pushing from attractant and repellent, when both are present) and move toward a preferred location (the other stream) and leave the channel at a different exit. As a result, viable cells are separated from dead ones.

Figure 13:
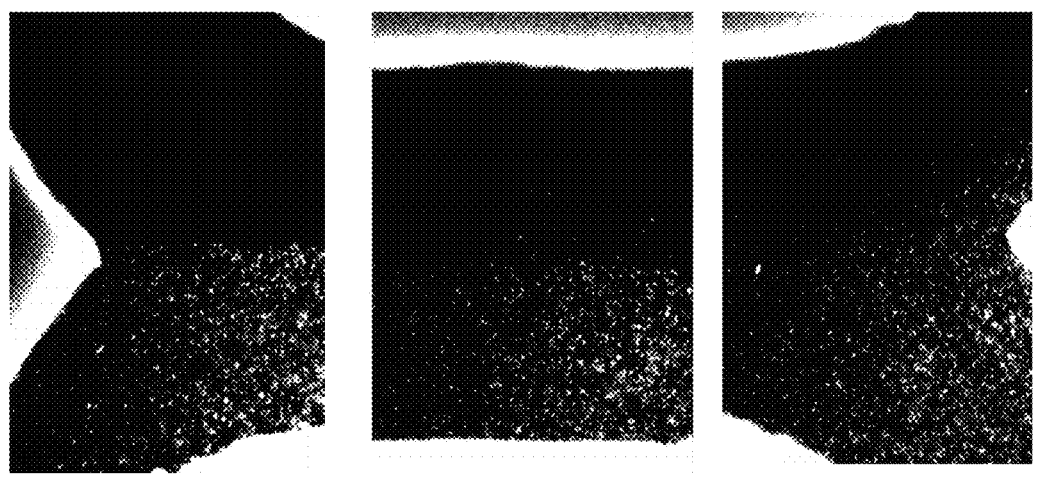
FIG. 13 depicts two streams of bacteria (dead cells) and buffer flowing independently in the central channel of the device depicted in FIG. 12.
Figure 14:
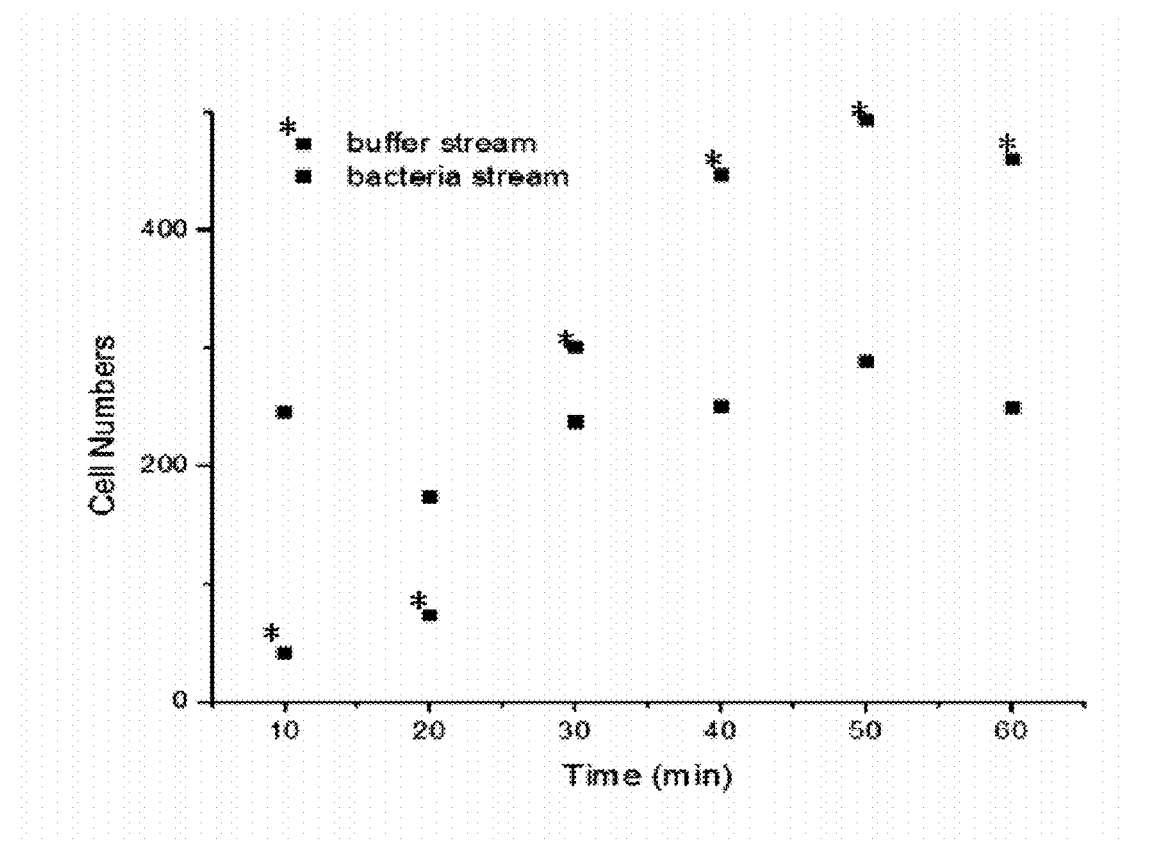
FIG. 14 depicts the results of samples taken at different time windows during assay the downstream portions of the device depicted in FIG. 12 for both a bacteria stream (squares) and a buffer stream (squares with *) and plate counted. More cells were obtained in the buffer stream after the cell sample was introduced in the system for 30 minute.
Figure 15:
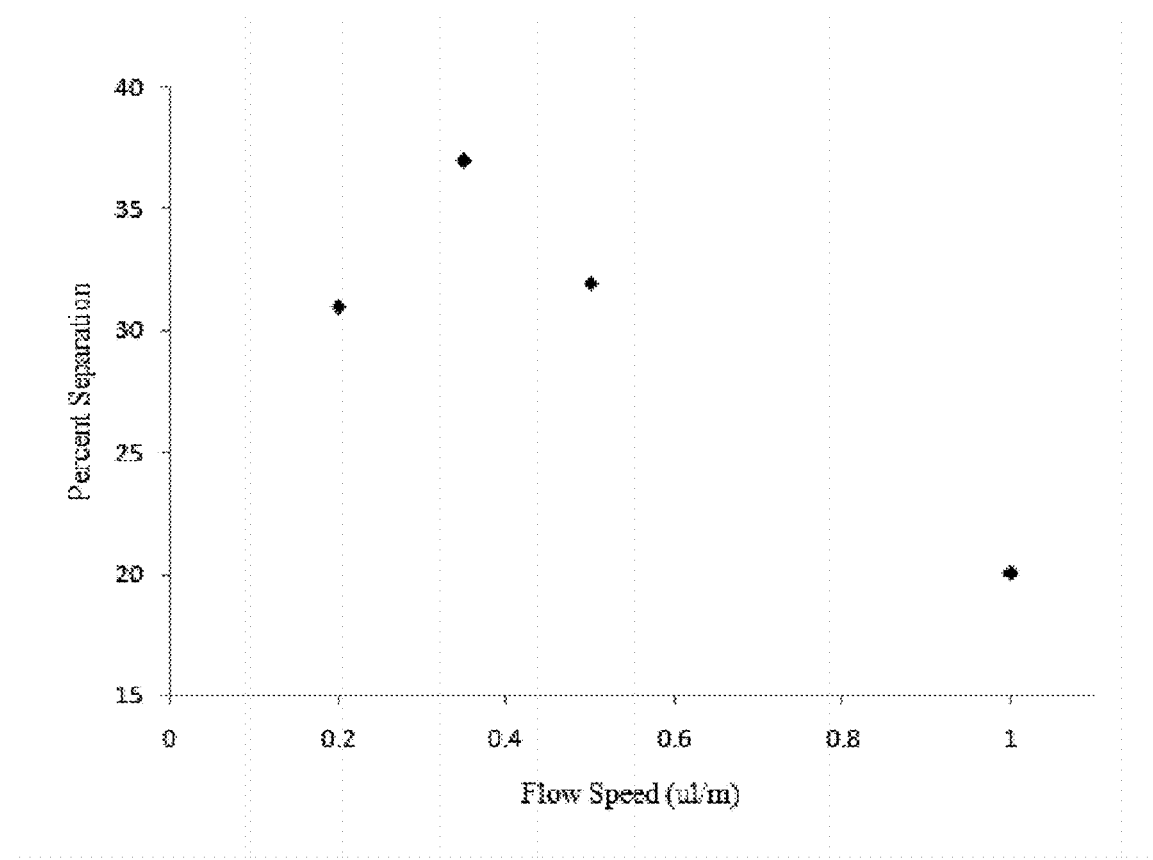
FIG. 15 depicts the percentage of live cells that moved from the sample channel to the buffer channel in 40 minutes at various flow speeds. Experiments were run using 10 mmol L-Aspartic Acid and 10 mmol Nickel Chloride in Tris buffer.
Figure 16:
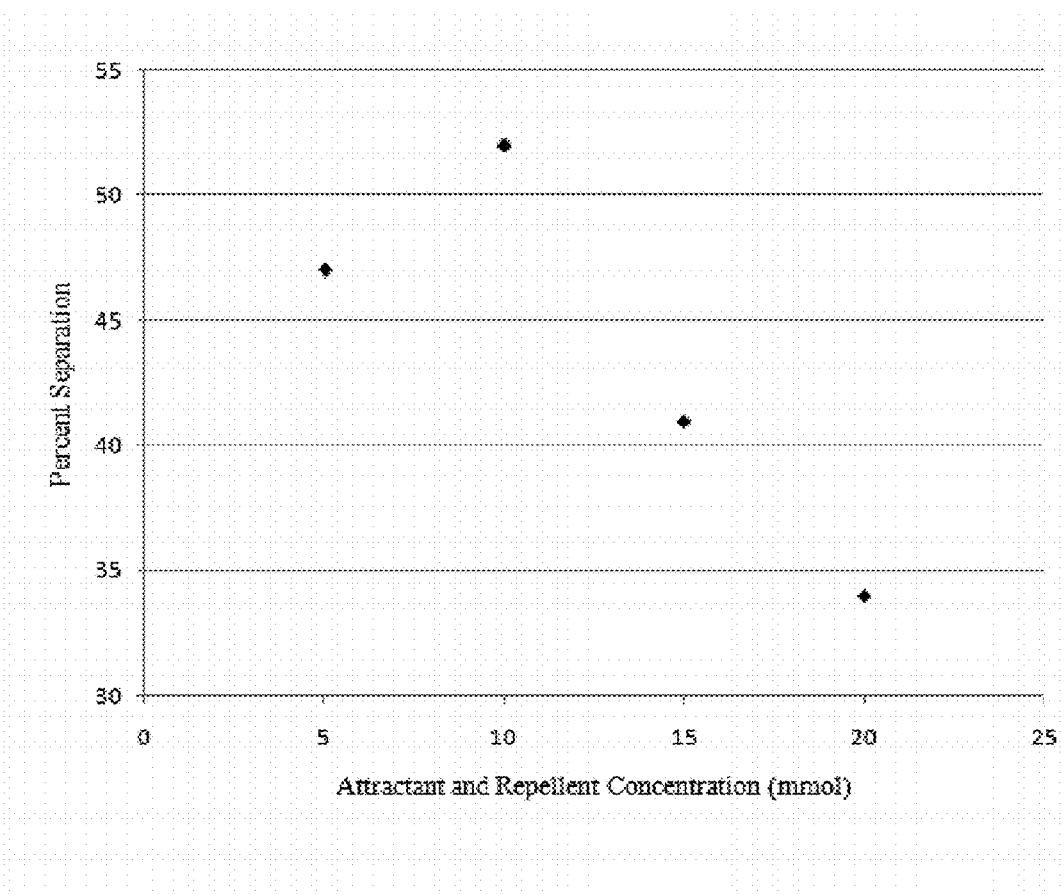
FIG. 16 depicts the percentage of live cells that moved from the sample channel to the buffer channel using various concentrations of attractant and repellent. These experiments used a flow speed of 0.35 ul/min and Tris buffer.
Figure 17:
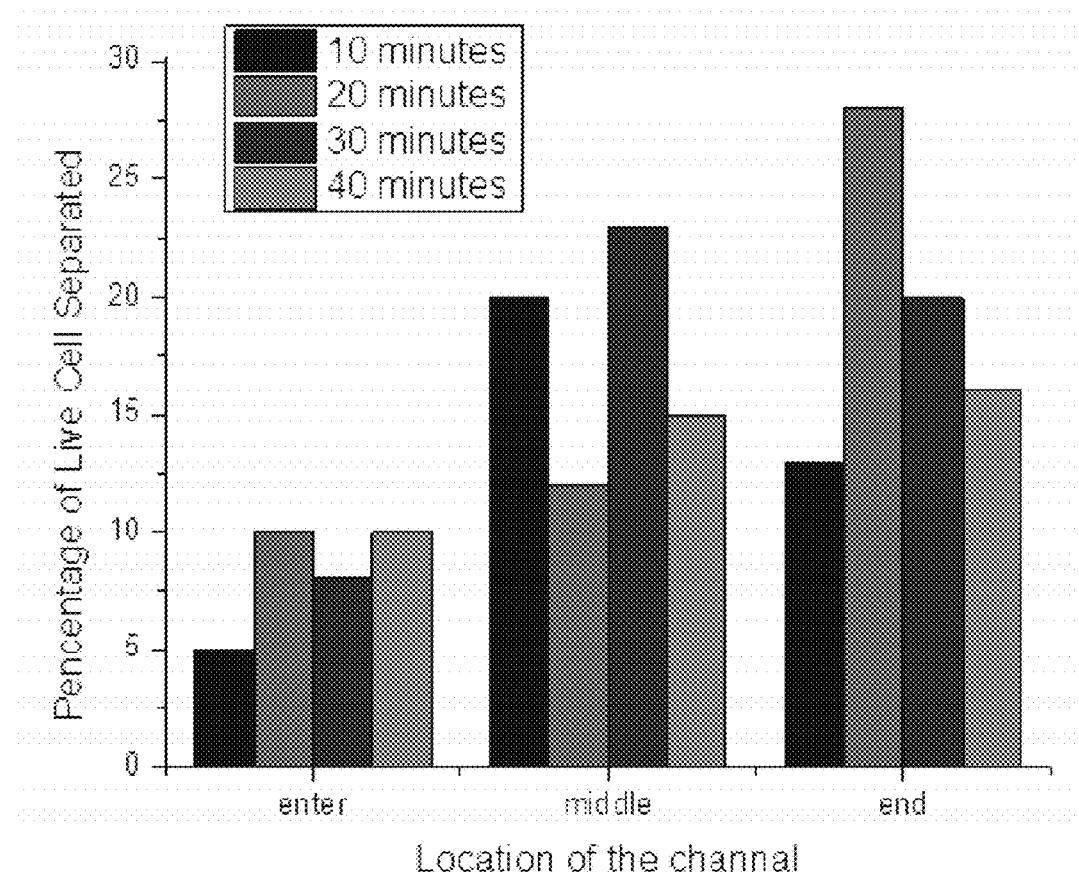
FIG. 17 depicts the mixture of live and dead cells introduced into the central channel for separation efficacy studies. Relative percentages of live cells present at the entrance, middle, and end of the central channel of the device over 10 minute increments (from left to right, beginning at 10 minutes and ending at 40 minutes) are provided.

Assays have shown that the stream of dead bacterial flow does not mix with the buffer stream. Pictures taken using the microscope at the beginning, middle and exit of the center channel were shown in FIG. 13, indicating a typical laminar flow in this channel. In contrast, with the application of chemoeffectors (aspartic acid as the attractant and $Ni^{2+}$ as the repellent) in the proposed design, up to 84% of the viable cells made the shift and exited in the buffer stream. The data can be seen in FIGS. 14-17. Both flow rate and concentration of chemoeffectors were investigated for effects on bacteria separation.

The above examples are included for illustrative purposes only and is not intended to limit the scope of the disclosure. Many variations to those methods, systems, and devices described above are possible. Since modifications and variations to the examples described above will be apparent to those of skill in this art, it is intended that this invention be limited only by the scope of the appended claims. One skilled in the art will appreciate further features and advantages of the presently disclosed methods, systems and devices based on the above-described embodiments. Accordingly, the presently disclosed methods, systems and devices are not to be limited by what has been particularly shown and described, except as indicated by the appended claims. All publications and references cited herein are expressly incorporated herein by reference in their entirety or for purposes of which they are specifically cited.

We claim:

1. A method for separating live and dead cells in a sample comprising a mixed population of live and dead cells, the method comprising:
    (a) providing a microfluidic device, the microfluidic device comprising:
        a first microfluidic channel comprising a laminar flow path, a first inlet positioned proximate a first end of the laminar flow path, a first outlet positioned proximate a second end of the laminar flow path, and a first static fluid collection chamber positioned adjacent to the laminar flow path;
        a second microfluidic channel comprising a second inlet and a second outlet; and
        a porous membrane disposed between the first and second microfluidic channels;
    (b) flowing the sample into the first inlet, through the laminar flow path, and out of the first outlet; and
    (c) flowing a first cellular stimulus into the second inlet, through the second microfluidic channel, and out of the second outlet, wherein at least a portion of the cellular stimulus diffuses out of the second microfluidic channel, through the porous membrane, and into the first microfluidic channel, thereby inducing a concentration gradient of the cellular stimulus such that the first static fluid collection chamber has a first concentration of cellular stimulus and the laminar flow path has a second concentration of cellular stimulus different from the first concentration,
    wherein the concentration gradient causes live cells in the sample to migrate from the laminar flow path into the first static fluid collection chamber.

2. The method of claim 1, wherein the cellular stimulus comprises a chemical.

3. The method of claim 1, wherein the cellular stimulus comprises a chemoeffector.

4. The method of claim 1, wherein the mixed population of live and dead cells comprises bacterial cells.

5. The method of claim 1, wherein the porous membrane has a pore size of less than 1.0 µm.

6. The method of claim 1, wherein the porous membrane has a pore size less than the size of the live cells such that the live cells are not capable of axial flow through the porous membrane.

7. The method of claim 6, wherein the porous membrane has a pore size large enough to ensure diffusion of the cell stimulus through the porous membrane.

8. The method of claim 1, wherein the microfluidic device comprises at least two static fluid collection chambers.

9. The method of claim 1,
    wherein the microfluidic device further comprises a third microfluidic channel comprising a third inlet and a third outlet,
    wherein the first microfluidic channel further comprises a second static fluid collection chamber, and
    wherein at least a portion of the porous membrane is disposed between the first and third microfluidic channels,
    the method further comprising:
        flowing a second cellular stimulus into the third inlet, through the third microfluidic channel, and out of third outlet, wherein at least a portion of the second cellular stimulus diffuses out of the third microfluidic channel, through the porous membrane, and into the first microfluidic channel, thereby inducing a second concentration gradient of the second cellular stimulus such that the second static fluid collection chamber has a third concentration of cellular stimulus and the laminar flow path has a fourth concentration of cellular stimulus that is different than the third concentration,
        wherein the second concentration gradient causes live cells in the sample to migrate from the laminar flow path to the second static fluid collection chamber.

10. The method of claim 1 further comprising harvesting the migrated live cells from the microfluidic device.

11. The method of claim 1, wherein the concentration gradient comprises at least one of a chemical gradient, and electrical gradient, and a temperature gradient.

12. The method of claim 1, wherein the mixed population of live and dead cells comprises an unknown concentration of live cells and an unknown concentration of dead cells.

13. The method of claim 1, wherein the concentration gradient of the cell stimulus does not influence migration of the dead cells.

14. The method of claim 1, further comprising causing at least a portion of the dead cells to flow out of the first outlet.

15. The method of claim 1, wherein migration of the live cells to the static fluid collection chamber results in a greater concentration of live cells in the static fluid collection chamber than in the sample.

16. The method of claim 1, wherein the cellular stimulus comprises an attractant, and wherein the first concentration of cellular stimulus is greater than the second concentration of cellular stimulus.

17. The method of claim 1, wherein the cellular stimulus comprises a repellant, and wherein the second concentration of cellular stimulus is greater than the first concentration of cellular stimulus.

18. The method of claim 1, wherein the live cells include a viable pathogen and wherein the dead cells include a non-viable pathogen.

\* \* \* \* \*